United States Patent
Okerlund et al.

(10) Patent No.: US 9,629,587 B2
(45) Date of Patent: Apr. 25, 2017

(54) SYSTEMS AND METHODS FOR CORONARY IMAGING

(71) Applicant: General Electric Company, Schenectady, NY (US)

(72) Inventors: Darin Robert Okerlund, Waukesha, WI (US); Sandeep Dutta, Waukesha, WI (US); Brian Edward Nett, Waukesha, WI (US); David Pazzani, Waukesha, WI (US); Daniel Stassi, Milwaukee, WI (US); Tal Gilat Schmidt, Whitefish Bay, WI (US)

(73) Assignee: General Electric Company, Schenectady, NY (US)

( * ) Notice: Subject to any disclaimer, the term of this patent is extended or adjusted under 35 U.S.C. 154(b) by 203 days.

(21) Appl. No.: 14/511,875

(22) Filed: Oct. 10, 2014

(65) Prior Publication Data
US 2016/0012613 A1 Jan. 14, 2016

Related U.S. Application Data

(60) Provisional application No. 62/023,086, filed on Jul. 10, 2014.

(51) Int. Cl.
*G06T 11/00* (2006.01)
*A61B 5/00* (2006.01)
(Continued)

(52) U.S. Cl.
CPC .......... *A61B 5/7292* (2013.01); *A61B 5/7289* (2013.01); *A61B 6/00* (2013.01);
(Continued)

(58) Field of Classification Search
CPC .............. G06T 11/003; G06T 11/005; G06T 2207/10081; G06T 2207/30048;
(Continued)

(56) References Cited

U.S. PATENT DOCUMENTS

| 6,718,604 B1 | 4/2004 | Taga et al. |
| 8,175,356 B2 | 5/2012 | Movassaghi et al. |

(Continued)

OTHER PUBLICATIONS

Hoffmann et al., "Automatic determination of minimal cardiac motion phases for computed tomography imaging: initial experience", 2006, European Radiology16: 365-373.*
Leipsic et al., "Effect of a novel vendor-specific motion-correction algorithm on image quality and diagnostic accuracy in persons undergoing coronary CT angiography without rate-control medications", 2012, Journal of Cardiovascular Computed Tomography 6, 164-171.*

(Continued)

*Primary Examiner* — Katrina Fujita
(74) *Attorney, Agent, or Firm* — Dean D. Small; The Small Patent Law Group, LLC

(57) ABSTRACT

A method is provided including determining at least one range of phases of a cardiac cycle from which to select a selected phase based on at least one of patient demographic information, patient physiological information, or a general physiological model. The method also includes generating corresponding intermediate images for each of the phases of the at least one range of phases. Further, the method includes selecting the selected phase based on at least one image quality (IQ) metric of the intermediate images. Also, the method includes generating an image for diagnostic use using imaging information from the selected phase.

13 Claims, 32 Drawing Sheets

(51) Int. Cl.
*A61B 6/00* (2006.01)
*G01R 33/20* (2006.01)

(52) U.S. Cl.
CPC ............ *G01R 33/20* (2013.01); *G06T 11/003* (2013.01); *G06T 11/005* (2013.01); *A61B 2576/023* (2013.01); *G06T 2207/10081* (2013.01); *G06T 2207/30048* (2013.01); *G06T 2207/30101* (2013.01); *G06T 2211/412* (2013.01)

(58) Field of Classification Search
CPC .... G06T 2207/30101; G06T 2211/412; G01R 33/20; A61B 5/7289; A61B 5/7292; A61B 6/00; A61B 2576/023
See application file for complete search history.

(56) References Cited

U.S. PATENT DOCUMENTS

| | | | |
|---|---|---|---|
| 8,520,917 B2 | 8/2013 | Hayes et al. | |
| 2013/0051643 A1* | 2/2013 | Jackson | G06T 11/006 382/131 |
| 2014/0192951 A1 | 7/2014 | Kohara | |

OTHER PUBLICATIONS

Leschka et al., "Image Quality and Reconstruction Intervals of Dual-Source CT Coronary Angiography", 2007, Investigative Radiology, vol. 42, No. 8, 543-549.*

Seifarth et al., "Automatic selection of optimal systolic and diastolic reconstruction windows for dual-source CT coronary angiography", 2009, European Radiology 19: 1645-1652.*

Coronary CT angiography: automatic cardiac-phase selection for image reconstruction. Balazs Ruzsics, European Radiology Aug. 2009, vol. 19, Issue 8, pp. 1906-1913.

Automatic phase determination for retrospectively gated cardiac CT. Manzke R1, Med Phys. Dec. 2004;31(12):3345-3362.

Kymogram detection and kymogram-correlated image reconstruction from subsecond spiral computed tomography scans of the heart. Kachelrie, M, Sennst, Medical Physics. 2002; 29(7): 1489.

Raw data-based detection of the optimal reconstruction phase in ECG-gated cardiac image reconstruction. D. Ertel, M. Kacheirie, Med. image Comput. Comput. Assist. Intervention, 2006;9(Pt 2):348-55.

Improving best-phase image quality in cardiac CT by motion correction with MAM optimization. Rohkohl C, Med Phys. 2013; 40(3):031901.

* cited by examiner

SYSTEMS AND METHODS FOR CORONARY IMAGING

RELATED APPLICATIONS

The present application makes reference to and claims priority to U.S. Provisional Application No. 62/023,086, filed Jul. 10, 2014, entitled "Systems and Methods for Coronary Imaging," the entire subject matter of which is incorporated by reference herein.

BACKGROUND OF THE INVENTION

The subject matter disclosed herein relates generally to systems and methods for computed tomography (CT) imaging, and for coronary imaging using CT.

In CT imaging, an X-ray source may be rotated around an object to obtain imaging information. X-rays from the source attenuated by the object may be collected or detected by a detector and used to reconstruct an image. Motion of an object being imaged may present challenges to CT imaging. One example of an object to be imaged that may experience motion during CT imaging is a heart of a human patient. For example, cardiac motion may blur the coronary arteries in coronary CT angiography images, making it difficult for clinicians to perform an accurate diagnostic interpretation.

Reconstructing a cardiac volume at a phase of the cardiac cycle with the least motion may provide cardiologists with a more accurate representation of the coronaries; however, generating images at a multitude of cardiac phases and evaluating each of them to find the optimal phase creates a workflow problem for clinicians. Further, finding the best phase for different vessels may be difficult and time consuming for users if performed manually, resulting in relatively large expenditures of time and resulting in errors or inaccuracy. Conventional approaches may employ the use of default of standard or default phases or, alternatively, have a user manually select a phase. Manual selection may be time-consuming, while use of standard or default phases may be prone to error or unreliability, for example to patient variability.

To obtain a CT image of the heart, a practitioner may attempt to identify a particular phase (e.g., a most quiescent phase) of the heart and generate an image at that phase. However, selection of a most quiescent phase may be quite challenging, requiring expertise on the part of the practitioner and/or resulting in improper selection. For example, variability between patients and/or between different times of acquisition for the same patient may provide challenges to selecting a phase or performing other aspects of coronary CT imaging. Further, selection of a phase by a practitioner may be a time-consuming and/or labor intensive effort. Further still, manual selection may result in increased radiation dose and/or increased contrast agent dose.

BRIEF DESCRIPTION OF THE INVENTION

In one embodiment, a method is provided that includes determining at least one range of phases of a cardiac cycle from which to select a selected phase (e.g., for final imaging or image reconstruction) based on at least one of patient demographic information, patient physiological information, or a general physiological model. The method also includes generating corresponding intermediate images for each of the phases of the at least one range of phases. Further, the method includes selecting the selected phase based on at least one image quality (IQ) metric of the intermediate images. Also, the method includes generating an image for diagnostic use using imaging information from the selected phase.

In another embodiment, a method is provided that includes generating corresponding intermediate images for each phase of at least one range of phases of a cardiac cycle. The method also includes determining a first image quality (IQ) metric for the intermediate images corresponding to IQ of through-plane vessels. Further, the method includes determining a second IQ metric for the intermediate images corresponding to IQ of in-plane vessels. Also, the method includes selecting a selected phase for final imaging from the at least one range of phases based on the first IQ metric and the second IQ metric for the intermediate images.

In another embodiment, an imaging system includes an acquisition unit and at least one processing unit. The acquisition unit includes an X-ray source and a computed tomography (CT) detector. The at least one processing unit is operably coupled to the acquisition unit and is configured to acquire CT imaging information from the acquisition unit. The at least one processing unit is further configured to determine at least one range of phases of a cardiac cycle from which to select a selected phase based on at least one of patient demographic information, patient physiological information, or a general physiological model; generate corresponding intermediate images for each of the phases of the at least one range of phases using the CT imaging information; select the selected phase based on at least one image quality (IQ) metric of the intermediate images; and generate an image for diagnostic use using imaging information from the selected phase.

DETAILED DESCRIPTION OF THE INVENTION

Figure 1:
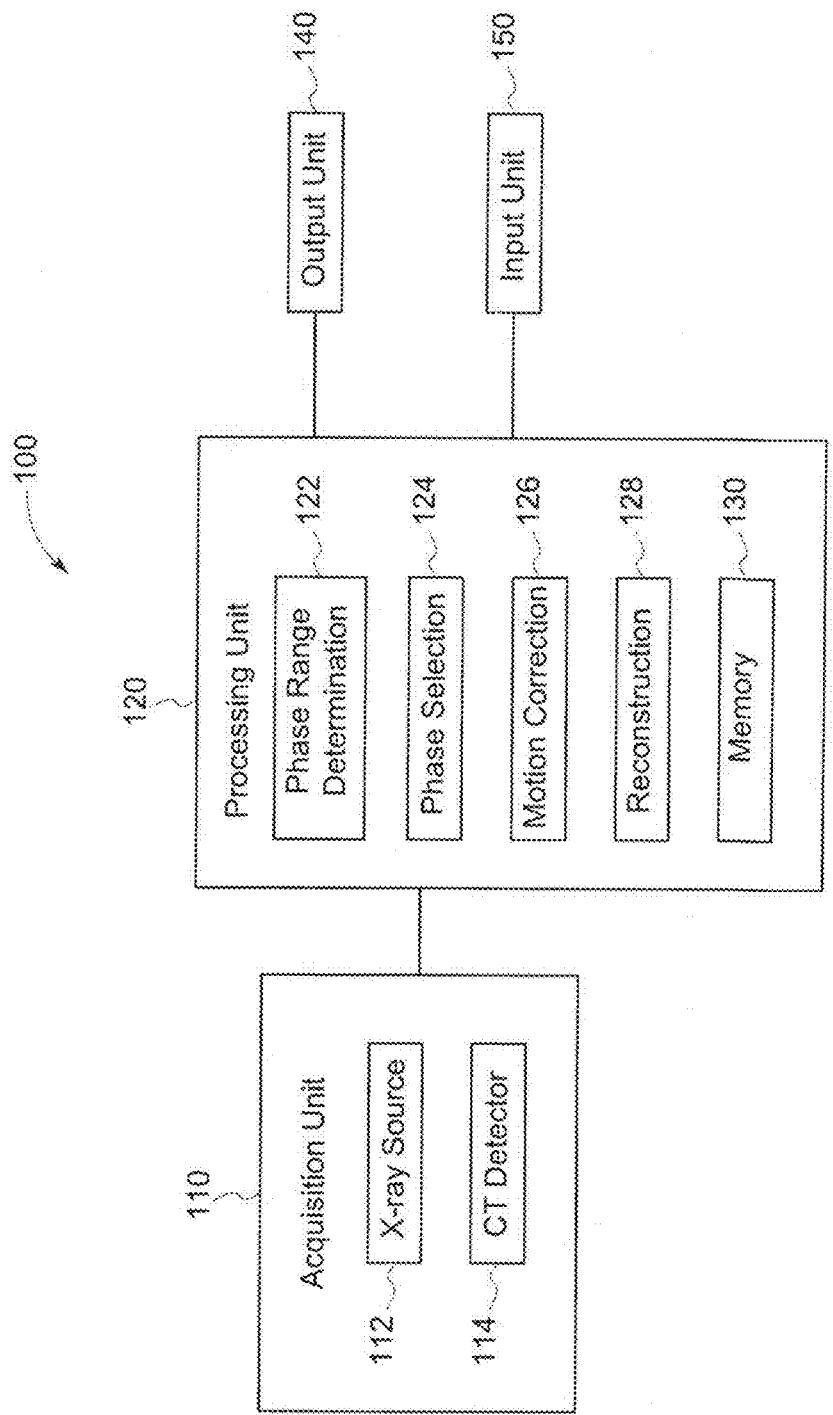
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for generating optimal coronary images, for example, by optimizing one or more aspects of an imaging workflow such as scan acquisition, image reconstruction, and image post-processing. Various embodiments provide for improved functioning of various aspects of an imaging workflow and improved cooperation or symbiosis among the various aspects (e.g., scan acquisition, image reconstruction, and image post-processing). Prospective information (e.g., patient heart statistics or other information obtained before performance of a CT scan), retrospective information (e.g., data acquired during a CT scan), and motion correction (e.g., intelligent motion correction and/or boundary registration) may be utilized to determine an optimal phase location within the cardiac cycle and/or to address any motion in a selected phase (or phases) to maximize or improve image quality of coronary images. In various embodiments, the workflow may be automated, for example, starting with the positioning of a patient on a CT table, and continuing through generating final optimized coronary images (e.g., on a display of workstation) for review by a clinician.

In various embodiments, workflow complexities for coronary CT imaging are reduced. Further, the radiation and/or contrast dose efficiencies may be improved by optimizing one or more of prospective, retrospective, or post-processing (e.g., motion correction) components or aspects of a coronary CT imaging workflow. For example, radiation dose may be reduced by acquiring CT imaging information only over a predetermined or pre-selected range or ranges of phases identified as being more likely to include an ideal or optimal phase for imaging. For example, if it is predetermined that an ideal or optimal phase is most likely to occur within a 40%-50% range of a cardiac cycle, X-rays may only be provided and detected over the 40%-50% range.

With respect to the prospective aspects, for example, an acquisition may be optimized or improved by considering one or more factors or aspects prior to performing a scan, for example to select a range of phases for consideration as a selected phase for image reconstruction. As one example, clinically relevant physiological models may be considered in selecting a range of phases for consideration. As another example, patient disease history and/or one or more clinical indications may be considered in selecting a range of phases for consideration. As one more example, patient specific physiological and/or demographic parameters (e.g., heart rate (HR), or body mass index (BMI), among others) may be considered in selecting a range of phases for consideration. The particular relationships between physiological parameters and optimal phase ranges, and/or the models utilized in determining optimal phase ranges, may be based on historical information or information obtained in clinical studies.

Once a range (or ranges) of phases has (or have) been determined from which to select a selected phase (e.g., a phase to be used for final imaging or image reconstruction, and/or for further analysis by a practitioner), a scanning operation may be performed to acquire CT information limited to or substantially limited to the determined ranges. For example, an X-ray source and CT detector may be operated to collect information based on the determined range. The operation of the X-ray source and CT detector may be triggered on and off based on information from an EKG of a patient being scanned. For example, if the determined range to be acquired is for 40-50% of the R-R cycle, the X-ray source and CT detector may be triggered to start acquiring information at a time that is about 40% of the duration of the R-R cycle after a detected R wave and to stop acquiring information at about 50% of the duration of the R-R cycle after the detected R wave. A time lag from triggering of the source and detector to actual operation of the source and detector may be factored into the times selected for starting and stopping the imaging information acquisition. By triggering an X-ray source and collecting CT information only for a predetermined range (or ranges), the total radiation dose may be reduced compared to techniques collecting CT information over an entire cardiac cycle (or cycles).

The retrospective aspects in various embodiments may relate or correspond to the selection of an optimal phase to be used for image reconstruction based on information obtained during a scan. The reconstructed image from the selected phase may be utilized for diagnostic purposes by a practitioner. For example, a system (e.g., one or more processors of a system) may automatically or autonomously select an optimal phase for image reconstruction from the range of phases for which data was acquired (e.g., the range of phases specified by the prospective aspect). For example, a subset of images at various increments of phases within the acquired phase range may be automatically generated. Then, an algorithm may be run that evaluates a cost-function that finds the most optimal phase for the purpose of the study. These images may be understood as intermediate images, and the retrospective aspect may be understood as an intermediate aspect. In some embodiments, the intermediate images may be full fidelity images, while in other embodiments the intermediate images may be less than full or lower fidelity images.

For example, less than full or lower fidelity images as used herein may not have a sufficient fidelity for diagnostic use by a practitioner. In some embodiments, one or more reconstruction steps may be turned off or not utilized in generating the intermediate images. In some embodiments, the intermediate images may be for an entire volume that will be imaged in a final image or reconstructed image to be used for diagnostic purposes, while in other embodiments, the intermediate images may be for only a part of the volume (e.g., less than 100% of the volume). In some embodiments, the intermediate images may be generated utilizing sparse sampling of the volume. Further, when generating the intermediate images, one or more of a different image size matrix, thicker slice thickness, or larger image intervals may be employed relative to generation of images to be reconstructed and/or used for analysis or diagnosis. In some embodiments, an advance model or atlas-based logic may be employed to analyze certain relevant, pertinent, or important anatomical locations with the volume. In some embodiments, synthesized images from basic full fidelity images (or from lower fidelity images) may be employed in generating the intermediate images. The intermediate image sets, after generation, may be used as an input to an image analysis algorithm to determine a selected (e.g., most optimal) phase for final imaging or image reconstruction. Image analysis algorithms in various embodiments may utilize a cost function that considers one or more of motion, contrast, image quality (e.g., signal to noise ratio (SNR) or other image quality metric), and determine a phase or phases having the least motion or otherwise providing an ideal, optimal, or preferred phase for final imaging or image reconstruction.

In some embodiments, an Auto Phase Detection Algorithm may be employed that retrospectively develops an image metric for quantifying the phase with the least motion for single-beat coronary CT angiography exams. In some embodiments, for each phase (e.g., each phase within a range selected based on prospective information), a metric is calculated that directly quantifies coronary image quality in a subset of reconstructed images (e.g., intermediate images as discussed herein). The metric may be based on the circularity and edge strength of through-plane vessels as well as the edge strength of in-plane vessels. A combination of a through-plane metric and an in-plane metric may be used, with the particular combination configured based on clinical needs, for example. The particular relationships or metric used may vary by use or application. In some embodiments, the best phase for imaging or phase having the least motion may be selected as the phase having the highest through-plane vessel score while still having an acceptable in-plane vessel score (e.g., satisfying an in-plane threshold). It may be noted that image quality (IQ) metrics as used herein may be evaluated on a phase by phase basis, in contrast to approaches that compare one or more aspects of two or more phases.

In various embodiments, an automatic phase detection (or selection) algorithm may consist of two independently-calculated metrics that quantify image quality (IQ). The metrics may be evaluated jointly to select the best phase for reconstruction. For example, vessels may be categorized into two types—in-plane (e.g., extending generally along a plane of an image) and through-plane vessels (e.g., extending generally into a plane of an image). A through-plane metric quantifies IQ for vessels travelling longitudinally through the volume. Circular cross-sections of the vessels will be visible in each axial image. Blurring caused by motion artifacts makes vessels appear less circular with softer edges. Thus, the through-plane metric may be based on the circularity and edge strength of the vessels. The through-plane metric may be calculated for all phases of interest (e.g., all phases identified based on prospective information).

The in-plane metric in various embodiments quantifies IQ of vessels travelling along the transverse plane. The shape of the vessels varies considerably due to branches and turns. Blurring due to motion will cause the edges of these vessels to be softer. Because the vessels are travelling in-plane, the in-plane vessels will be present in a small slab of data. The in-plane metric may identify this slab of data and calculate IQ based on vessel edge strength. In some embodiments, the in-plane metric may be converted to an acceptability metric by comparing the relative in-plane scores from a small range of phases. In various embodiments, an acceptability threshold may be altered to accept more or fewer in-plane scores.

In some embodiments, the phases may be ranked based on through-plane metrics from a phase having the best through-plane metric to a phase having the worst through-plane metric, with the phases than checked in order for satisfaction of the in-plane metric, starting with the phase having the best through-plane metric. Once a phase having an acceptable in-plane metric is identified as the phases are checked in such an order, the first phase encountered having an acceptable in-plane metric may be selected. Thus, the phase having the highest through-plane metric, while still satisfying an in-plane threshold (e.g., having an acceptable in-plane metric), may be selected as the best phase, or the phase for final imaging and/or diagnostic analysis. In some embodiments, when the next best through-plane phase is substantially lower than the best through-plane metric (e.g., the next best is 75% or less of the best), and when no phase has yielded acceptable in-plane vessels, the acceptability threshold for the in-plane metric may be decreased. The in-plane check may then be repeated, starting with the phase having the best through-plane metric, or the best through-plane phase. In some embodiments, the acceptability threshold may be adaptively adjusted based on whether motion correction will be applied.

In various embodiments, one or more of a number of parameters may be used to control or configure the resolution and performance of the metric calculations. The parameters may be used (e.g., selected, modified, displayed, or the like) interactively through real-time interactions on a Graphical User Interface (GUI) by a user. For example, the threshold of acceptability of in-plane vessels could be adjusted by a user on a case-by-case basis if a user so desires. Guidance in selecting or adjusting the threshold of acceptability may be displayed to the user. Similarly, in some embodiments, from a GUI displaying a localizer image, the number, location, and spacing of slices to be analyzed by an algorithm to determine the metrics may be set by the user. In various embodiments, a user may also elect to see the best image for a particular vessel, or may elect to see an acceptable IQ for all vessels in one image. It may be noted that values of parameters used in the determination of one or more ranges of phases for further evaluation and/or used in the selection of a best phase, whether selected automatically and/or manually, may be varied to allow for tailoring of the selection of the best phase for a given patient or procedure (e.g., a first group of parameters may be used for selecting a best phase for use in connection with evaluating a first vessel and/or clinical task, while a second group of parameters may be used for selecting a best phase for use in connection with a second vessel and/or clinical task).

It may be noted that one or more aspects or steps of various embodiments may be run in the same or different portions of a system. For example, various aspects may be performed at a CT console, an image processing workstation, or a combination of both. Accordingly, various embodiments provide for flexibility regarding where one or more aspects are implemented in a system. Further, the selection of an optimal phase (or phases) may be readily extended to multi-beat acquisitions. For example, an optimized phase for each heart cycle may be selected.

With respect to the post-processing or motion correction aspects, once an optimal phase has been determined, a full fidelity image reconstruction for that phase may be automatically generated and made available for viewing by a practitioner or clinician (e.g., radiologist). In some embodiments, when the best phase selected has a significant amount of residual motion (e.g., as determined using an appropriate motion metric), coronary motion correction may be adaptively applied. For example, all necessary data for motion correction may be automatically generated prior to display of a full fidelity image to the practitioner or clinician. In some embodiments, when the selected phase satisfies a predetermined minimum IQ or target IQ (e.g., based on one or more IQ metrics), motion correction may not be performed, but if the selected phase does not satisfy the predetermined minimum IQ, motion correction may be performed. By performing motion correction when the target IQ is not satisfied, a usable or otherwise improved image may be provided, while, by not performing motion correction when the target IQ is satisfied, computational resources and time to reconstruct an image may be reduced.

Various embodiments provide improved CT coronary imaging. A technical effect of at least one embodiment includes improvement of CT imaging workflow. A technical effect of at least one embodiment includes improved radiation and/or contrast dose efficiency of cardiac CT exams. A technical effect of at least one embodiment includes removal or minimization of manual steps in coronary CT imaging. A technical effect of at least one embodiment includes optimization of acquisition ranges, and elimination or reduction of re-scanning or acquisition of information for more phases of data than is necessary. A technical effect of at least one embodiment includes reduced time in analysis of obtained images (e.g., coronary CT images). A technical effect of at least one embodiment includes improved tailoring of phase selection for each particular patient. A technical effect of at least one embodiment includes providing a motion-based image quality metric (or metrics) that separately considers through-plane and in-plane vessels and/or separately considers right and left side vessels of the heart. A technical effect of at least one embodiment includes addressing unique clinical needs, for example to select a best image of a particular vessel (e.g., a best image of a proximal right coronary artery to assess a stent). A technical effect of at least one embodiment includes providing the flexibility for a user to select a best phase for imaging an individual vessel or group of vessels, for example a phase where all vessels are acceptable but may not be the best phase for vessels that are not in the individual vessel or group of vessels. A technical effect of at least one embodiment includes improving diagnostic confidence and reliability.

FIG. 1 illustrates an imaging system 100 in accordance with an embodiment. The imaging system 100 may be configured, for example, to perform computed tomography (CT) scanning of an object, such as human or animal patient (or portion thereof). The imaging system 100 includes an acquisition unit 110 and a processing unit 120. Generally, the acquisition unit 110 is configured to acquire projection data or imaging data (e.g., CT data), and the processing unit 120 is configured to reconstruct images using the data acquired by the acquisition unit 110. The processing unit 120 may also be configured to select or determine phases of a cardiac cycle for which images will be reconstructed. In some embodiments, the processing unit 120 may control the acquisition unit 110 to acquire the CT information only for a range of phases from which a particular phase (or phases) will be selected for image reconstruction. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted acquisition unit 110 is configured as a CT acquisition unit, and includes an X-ray source 112 and a CT detector 114. (For additional information regarding example CT systems, see FIG. 32 and related discussion herein.) The X-ray source 112 and the CT detector 114 (along with associated components such as bowtie filters, source collimators, detector collimators, or the like (not shown in FIG. 1)) may rotate about a central axis of a bore of a gantry (not shown in FIG. 1) of the system 100.

Generally, X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed. For example, the input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a gantry bore and rotated about the object. As the X-ray source 112 rotates about the object during an imaging scan, X-rays received by the CT detector 114 during one complete rotation provide a 360 degree view of X-rays that have passed through the object. Other scanning ranges may be used in alternative embodiments. It may also be noted that an individual scout scan may be performed from a single orientation.

As indicated herein, the processing unit 120 is configured to reconstruct an image using information obtained via the acquisition unit 110. Further, the processing unit 120 is configured to determine a range (or ranges) of phases of a cardiac cycle over which to acquire CT imaging information, and to select a phase (or phases) from the determined range for which to generate a final image. The selected phase may be understood in various embodiments as a best phase or a phase for which the effects of motion on an image to be used for a clinical task are reduced, minimized, or eliminated.

The depicted processing unit 120 is operably coupled to the input unit 150, the output unit 140, and the acquisition unit 110. The processing unit 120, for example, may receive information before performance of a scan, referred to herein as prospective information, and determine an appropriate range of phases to analyze to identify a particular phase (e.g., a most quiescent phase) for imaging using the prospective information As another example, the processing unit 120 may receive imaging data or projection data, referred to herein as retrospective information, from the CT detector 114. The processing unit 120 may analyze the imaging data or projection information, for example using an algorithm or technique discussed herein, to identify a particular phase (or phases) to be used in final imaging or reconstruction of an image for use with diagnostic purposes from the previously determined range of phases. The processing unit 120 may provide control signals to one or more aspects of the acquisition unit 110, such as the X-ray source 112. The processing unit 120 may include processing circuitry configured (e.g., programmed) to perform one or more tasks, functions, or steps discussed herein.

In the illustrated embodiment, the processing unit 120 includes a phase range determination module 122, a phase selection module 124, a motion correction module 126, a reconstruction module 128, and a memory 130. It may be noted that other types, numbers, or combinations of modules may be employed in alternate embodiments, and/or various aspects of modules described herein may be utilized in connection with different modules additionally or alternatively.

The depicted phase range determination module 122 in the illustrated embodiment is configured to determine one or more ranges of phases from which a selected phase will be selected. The range of phases may be described in terms of a percentage of a duration of a cardiac cycle (e.g., a range of 50-60% corresponds to a timeframe beginning at the halfway point of a cardiac cycle and continuing for another 10% of the cardiac cycle.) The one or more ranges of phases may be selected based on a likelihood of the ranges containing a best single phase for imaging purposes, such as a phase having the least effect of motion on imaging relevant to a clinical task or objective. The phase range determination module 122 may determine the one or more ranges based on a general physiological model as modified by factors relating to an individual patient or procedure. For example, a wider range or ranges may be employed when there is greater heart rate variability. As another example, a range corresponding to end systole may be used for certain heart rates, while a range corresponding to mid-diastole as well as a range corresponding to end systole may be used for different heart rates.

The depicted phase selection module 124 is configured to select a particular phase (or phases) from the determined range (or ranges). The phase selection module 124 in the illustrated embodiment is configured to identify the phase that is least effected by motion (e.g., based on one or more image quality metrics). For example, an image (e.g., an intermediate image that may not necessarily have the fidelity of a final image) may be generated for each phase, and evaluated for image quality. In some embodiments, multiple image quality metrics (e.g., a first metric corresponding to through-plane vessels and a second metric corresponding to in-plane vessels as discussed herein) may be employed. Accordingly, in various embodiments the phase selection module 124 may select a phase based on actual image quality (e.g., the effects of motion) instead of based merely on a measured or otherwise determined motion or amount of motion. As used herein, a particular phase of a cardiac cycle (e.g., a phase selected by the phase selection module 124) may be understood as corresponding to a duration of time sufficient to collect enough imaging information to generate an image with sufficient fidelity for diagnostic purposes. For example, a phase may have a duration of one complete rotation or less of a CT scanner. The phase may be identified, for example, based on a percentage of time elapsed of a cardiac cycle (e.g., for a cardiac cycle having a period of 1 second, a phase identified as corresponding to 75% of a cardiac cycle may be a phase centered in time around 750 milliseconds after initiation of the cardiac cycle).

The depicted motion correction module 126 is configured to perform motion correction and/or other post-processing on a final image. The motion correction module 126 may be selectively activated based on an image quality metric determined by the phase selection module 124 in various embodiments. For example, if the IQ metric for the selected phase is relatively high, motion correction may not be required and motion correction information may not be collected. However, if the IQ metric for the selected phase is relatively low, motion correction may be more likely, and, in order to save overall process or workflow time, the motion correction information may be proactively collected during or shortly after imaging information acquisition and used to correct motion in a final image either before a request by a practitioner viewing the final image or responsive to a request by the practitioner.

The depicted reconstruction module 128 is configured to generate or reconstruct images using information acquired form the CT detector. For example, the reconstruction module 128 may be configured to generate intermediate images for use by the phase selection module 124, and/or reconstruct a final image based on the selected phase. Different settings may be used to generate or reconstruct the intermediate images and the final image. For example, additional steps may be used to reconstruct the final image than are used to generate the intermediate images. The final image, in some embodiments, may be reconstructed at a higher fidelity than the intermediate images.

The input unit 150 may be configured to receive input, such as input providing prospective information for use by the phase range determination module 122, or input that adjusts a parameter (e.g., a threshold) associated with one or more IQ metrics employed by the phase selection module 124. The input may specify patient characteristics, describe a clinical procedure or task, or the like. The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. For example, the input unit 150 may receive information from a scanning system or aspect thereof corresponding to a clinical procedure or task relating to the scan to be performed. As used herein, to "obtain" may include, for example, to receive.

The output unit 140 is configured to provide information to the user. The output unit 140 may be configured to display, for example, an intermediate image (e.g., an image used in determining which phase will provide the best image), or a final image. The output unit 140 may include one or more of a screen, a touchscreen, a printer, or the like. It may be noted that the input unit 150 and output unit 140 are depicted schematically as separate units in FIG. 1 for ease and clarity of illustration. Other arrangements are possible. For example, one or more aspects of the input unit 150 and/or the output unit 140 may be incorporated into a CT console, and/or one or more aspects of the input unit 150 and the output unit 140 may be incorporated into an imaging workstation.

Figure 2:
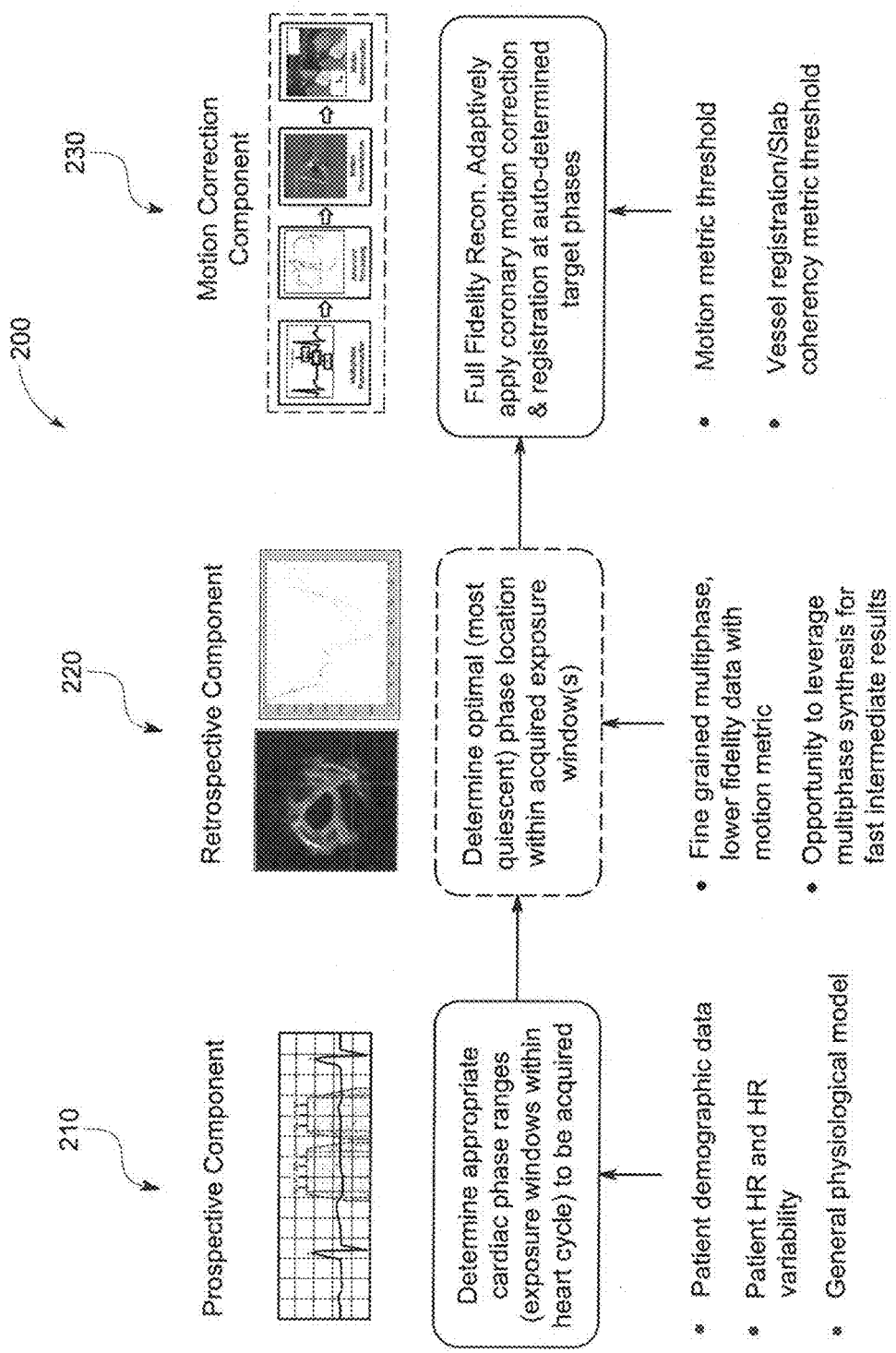
FIG. 2 provides a schematic view of a general framework for generating optimized coronary images during a clinical CT exam in accordance with various embodiments.

FIG. 2 provides a schematic view of a general framework 200 for generating optimized coronary images during a clinical CT exam in accordance with various embodiments. Generally, the framework 200 includes three primary components—a prospective component 210, a retrospective component 220, and a motion correction component 230.

The prospective component 210 may correspond to (e.g., be performed by or otherwise associated with) the phase range determination module 122 of the processing unit 120 in some embodiments. (It may be noted that a "component" as used herein may include or correspond to more than one module and/or physical entity, and/or portions of more than one module and/or physical entity.) Generally, the prospective component 210 provides for the determination of appropriate cardiac phase ranges (e.g., exposure windows within the heart cycle) to be acquired. For example, the range or ranges may be determined based on one or more of patient demographic information, patient heart rate, patient heart variability, or a general physiological model.

In various embodiments, a selected phase or phases for final image reconstruction will be selected from the determined cardiac phase range (e.g., the range determined using the prospective component 210) by the retrospective component 220. As indicated above, the appropriate range (or ranges) of cardiac phases may be determined based on one or more of patient demographic data, patient heart rate (HR) and HR variability, or a general physiological model. Generally, the determined phase range or ranges may be selected to include the portion or portions of the cardiac cycle that are likely to provide the best image for a particular application (e.g., the most quiescent phase) while limiting the phases of the cardiac cycle that are further evaluated by the retrospective component 220. The particular model or technique (or models or techniques) used to select the ranges may be based on physiological models. For example, empirical or experimentally based models may be developed, for instance as part of one or more clinical studies.

Figure 3A:
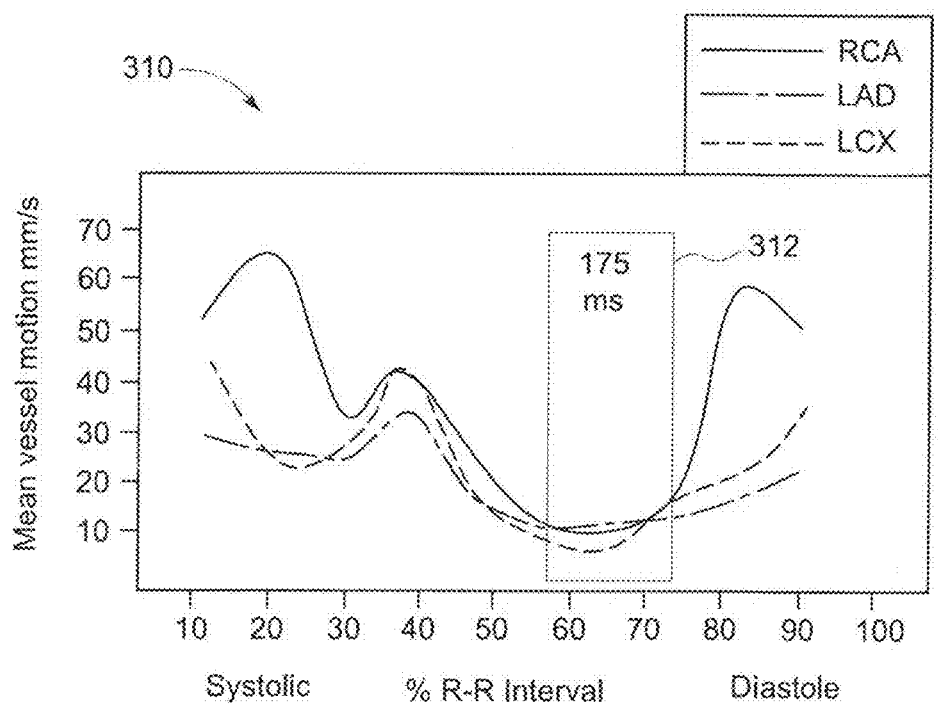
FIGS. 3A, 3B, 3C, 4, and 5 depict various aspects of a prospective component in accordance with various embodiments.
Figure 3B:
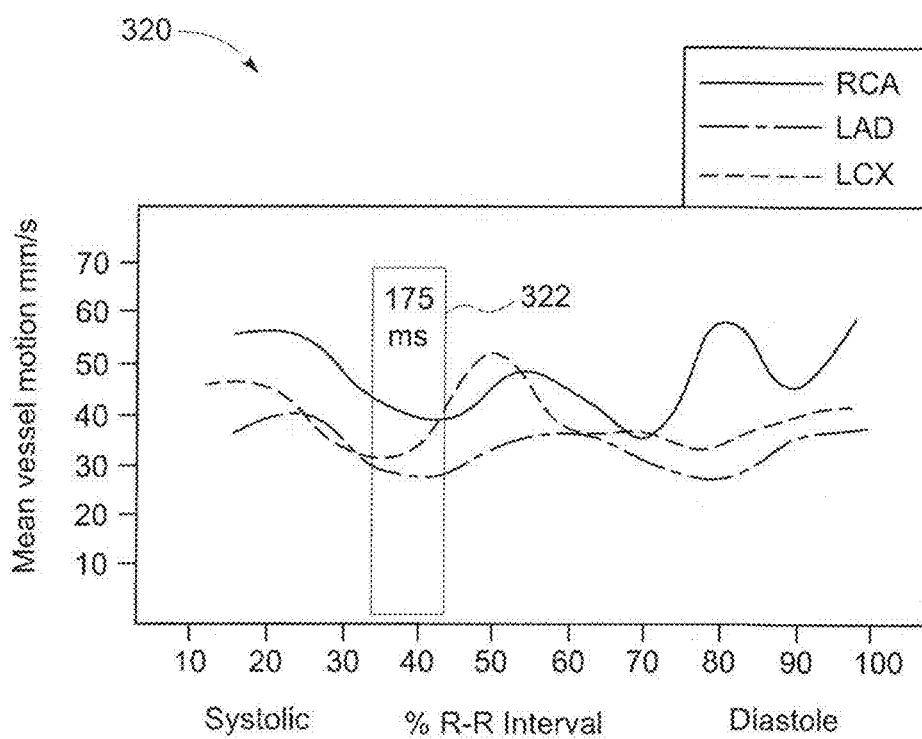
Figure 3C:
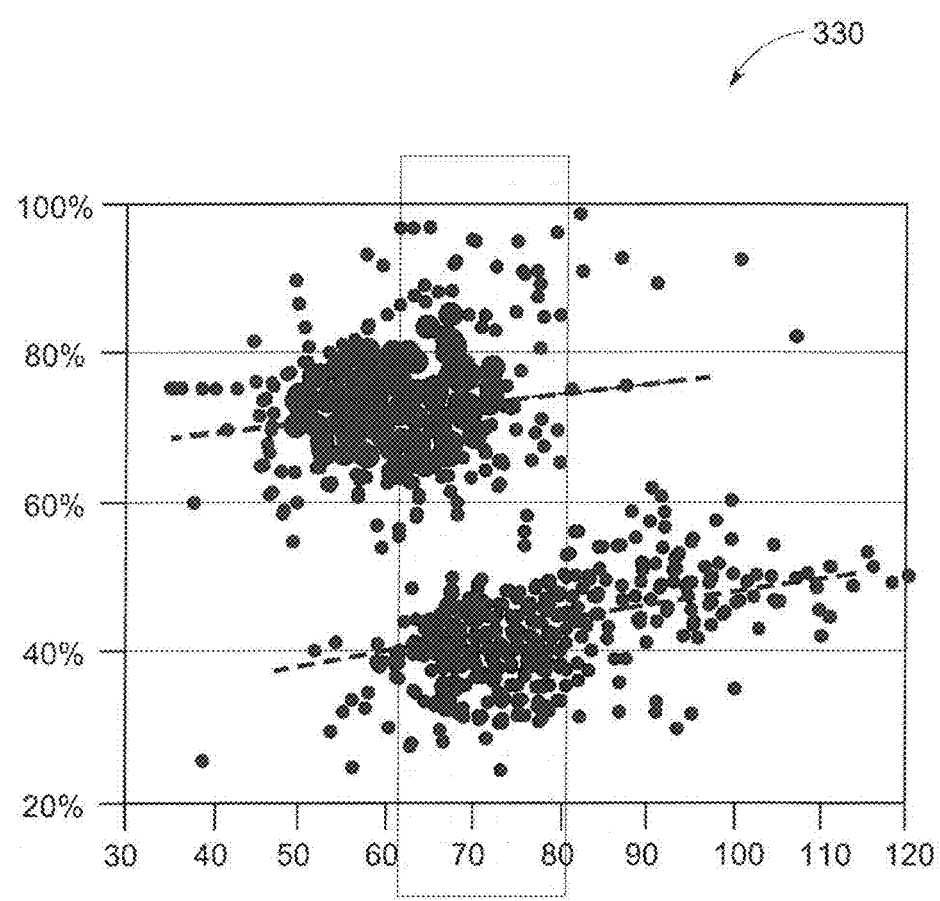
Figure 4:
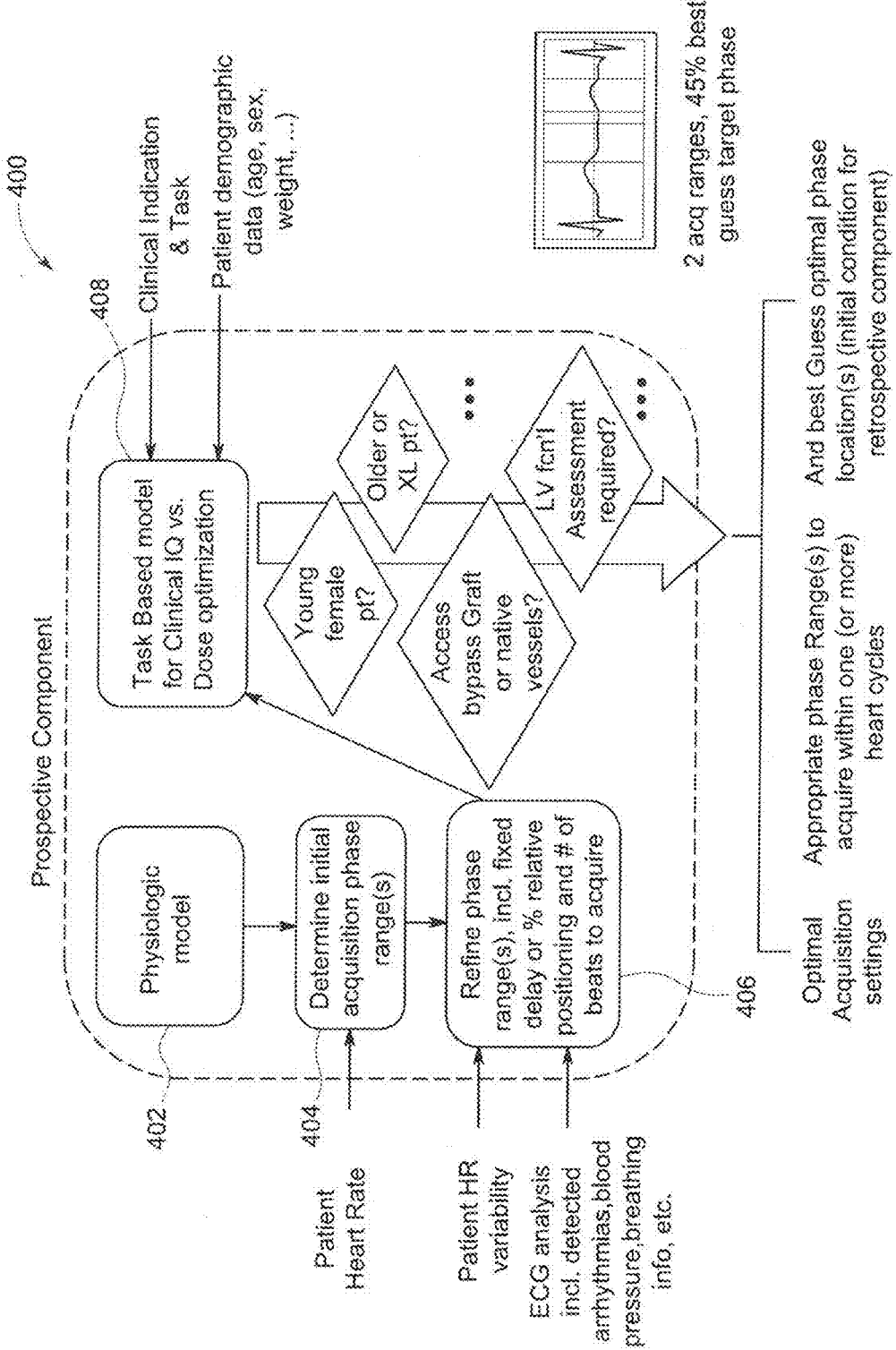
Figure 5:
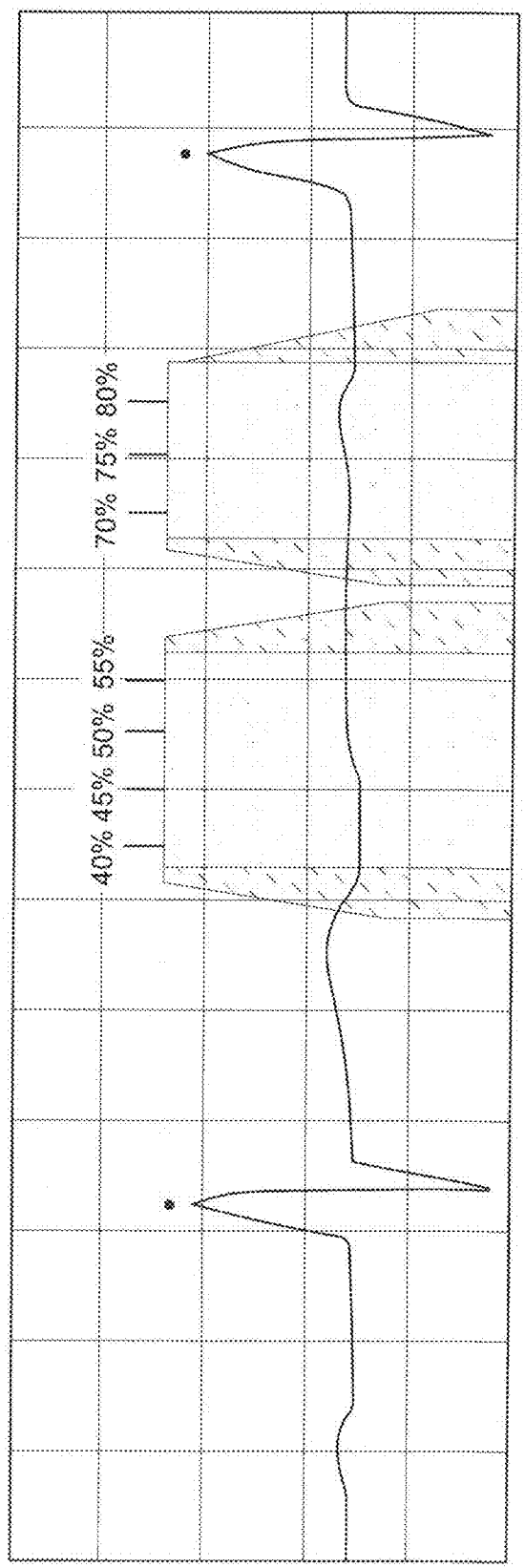

With reference to FIGS. 3-5, which describe various aspects of example embodiments of the prospective component, it may be noted that physiological models and/or patient specific information (e.g., weight, BMI, baseline heart rate information collected prior to the acquisition) may be utilized in various embodiments to determine the most suitable data acquisition window (or windows) that is (or are) appropriate for a given patient and procedure. The determination may specify, for example, how many phase ranges within the heart cycle for which CT data will be acquired, as well as what kind of CT imaging parameters will be used for the exam.

In various embodiments, patient modeling and specific information may be utilized to acquire the CT data in an optimal or improved fashion. For example, based on HR and HR variability determined prior to the acquisition, a system may determine an appropriate phase range or ranges to be acquired. In determining the range or ranges to be acquired, image quality and clinical robustness may be balanced against X-ray (and/or contrast) dose. As seen in FIG. 3A-3C, for example, different heart rates may correspond to different ranges. In the example embodiment, for a low heart rate, as seen at 310 in FIG. 3A, an ideal range 312 may be determined at mid-diastole, or about 70-80% of a cardiac cycle. For a high heart rate, as seen at 320 in FIG. 3B, an ideal range 322 may be determined at end-systole, or about 40-55% of a cardiac cycle. The ranges are also displayed in empirical model 330 of FIG. 3C. It should be noted that the particular model curves, ranges, and/or depictions of models of FIG. 3A-3C are meant by way of example for illustrative purposes only, and that other models may be employed in various embodiments. For example, the particular model used may be tailored for a particular application.

In one example implementation, the number of phase ranges to be acquired may be determined based on the HR, and the temporal duration of each phase range to be acquired may be adjusted based on the HR variation. For example, a higher HR variation may generally result in a longer temporal duration. Further, a system may adjust the range (or ranges) of acquisition within each group automatically based on patient information (e.g., age, sex, width, or the like, for example to emphasize a lower dose acquisition profile in a young, female patient) and clinical indication (e.g., if cardiac LV functional assessment is required).

FIG. 4 illustrates an example workflow 400 in accordance with various embodiments. At 402, a physiologic model is developed. The physiologic model may be developed empirically, for example based on historical information and/or clinical studies. The physiological model may correlate, for example, heart rate and/or heart variability, among others, with ideal phase ranges. At 404, an initial acquisition phase range or ranges is determined. The range or ranges, for example, may be determined using the physiologic model and based on heart rate of the patient. At 406, the phase range or ranges determined at 404 is refined. For example, the phase range or ranges may be revenged based on heart rate variability. Further, the determined and/or refined phase range may specify or take into account a delay (e.g., a delay between time of triggering acquisition of CT information and actual acquisition of CT information). Further still, the determined phase range may specify a percentage range stated as a percentage of a cardiac cycle, and may specify a number of beats or cycles over which to obtain CT information. The phase range may be determined and/or refined using information measured from a patient being scanned, such as an ECG analysis (including heart rate and/or heart rate variability), detected arrhythmias, blood pressure, breathing information, or the like. At 408, the phase range may be further refined, for example using a task based model for balancing image quality against radiation dose. The phase range, for example, may be refined based on patient type (e.g., the range may be reduced for a younger patient or other type of patient for which reduced dose is desirable) and/or clinical task or diagnostic purpose.

In the example seen in FIG. 5, 2 ranges are shown as the selected ranges—a first range between about 40 and 55% and a second range between about 70-80%. In the illustrated example, the heart rate may be an intermediate heart rate, for example about 77 beats per minute. The depicted phase ranges, for example, may correspond to the end-systole and mid-diastole phases, respectively, in the illustrated example (see FIG. 3). Generally, the acquisition ranges may be selected based on one or more of clinically relevant physiological models, patient disease history/clinical indication, or patient specific physiological and demographic parameters such as HR, BMI, or the like.

The retrospective component 220 may correspond to (e.g., be performed by or otherwise associated with) the phase selection module 124 of the processing unit 120 in some embodiments. In various embodiments, one or more algorithms may be employed utilizing IQ metrics to identify a particular phase to be used for final imaging from the determined range of phases (e.g., the range or ranges determined by the prospective component 230). With reference to the example embodiment described in FIG. 6, once an acquisition is completed of the determined range or ranges, a system may next, via the retrospective component 220, automatically determine a phase (e.g., the optimal phase or phase having the least effects of motion) for which to perform the final image reconstruction. The phase may be specified as a percentage of a cardiac cycle (e.g., a percentage of the duration of the cardiac cycle about which the phase is centered). Using both anatomical and physiological models, the selection may be accomplished by automatically generating a subset of images at various increments of phases within the acquired phase range. In some embodiment the increments may be in uniform temporal strides, while in other embodiments non-uniform temporal strides may be employed. Once the subset of images have been generated, an algorithm may be run to evaluate a cost-function to select the phase for imaging (e.g., the most optimal phase for the purpose of the study). In various embodiments, the cost function evaluation algorithm may be tailored to the clinical study need for the patient. For example, an automated algorithm may be utilized to find a cardiac phase with the minimum coronary vessel motion. Alternatively or additionally, the algorithm may be configured to detect a minimum or reduced amount of wall motion among the evaluated phases. The cost-function may also take into consideration one or more image parameters such as motion, contrast, SNR, or the like to provide a final selected phase.

Figure 6:
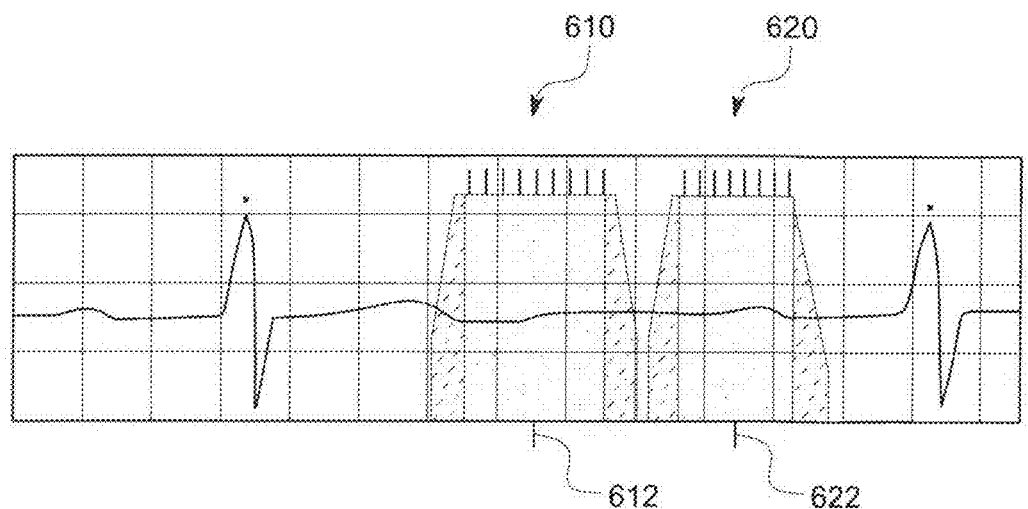
FIG. 6 describes various aspects of a retrospective component in accordance with various embodiments.

In the example embodiment of FIG. 6, a first range 610 and a second range 620 have been selected prospectively. Next, data from an acquisition (e.g., projection data, initial image data, intermediate image or other intermediate result) may be used to determine an optimal or preferred particular phase (or phases) for final imaging (e.g., reconstruction of one or more full fidelity images). In the depicted example, a first phase 612 is selected form the first range 610, and a second phase 622 is selected from the second range 620. For example, one or more image quality metrics may be determined for various phases using the data from the acquisition to select an optimal, ideal, or preferred phase (or phases) for final imaging. In some embodiments, final imaging of the selected phase (or phases) may include subsequent motion correction.

It may be noted that different types of images may be employed as the subset of images from which a phase will be selected. For example, in some embodiments, the intermediate images may be full fidelity images. As another example, one or more reconstruction steps (e.g., calibrations and/or corrections) may be turned off or not utilized in generating the intermediate images. Further, the intermediate images may be for an entire volume, while in other embodiments, the intermediate images may be for only a part of the volume (e.g., less than 100% of the volume). In some embodiments, the intermediate images may be generated utilizing more coarse or sparse sampling of the volume relative to final imaging. Further, when generating the intermediate images, one or more of a different image size matrix (e.g., 128×128, 256×256, or 512×512, among others), different slice thickness (e.g., thicker than used for final imaging), or larger image intervals (e.g., greater stride between adjacent image locations) may be employed relative to generation of images to be used for analysis or diagnosis. In some embodiments, an advanced model or atlas-based logic may be employed to analyze certain relevant, pertinent, or important anatomical locations with the volume (e.g., to apply greater sampling and/or resolution in the more relevant regions of the volume). As one more option, intermediate images may be synthesized from basic full fidelity images (or, in some embodiments, from lower fidelity images) on a console or image processing workstation.

The images for each exam may be generated at unique phase intervals optimized for a particular case based on a-priori modeling information. For example, robust methods may be developed to determine the optimal phase that may take as input images that have degraded physics based corrections. In addition to speeding up image reconstruction by removing steps, it may be desirable to perform fewer back projection steps. In some embodiments, synthesized images from basic full fidelity images (or from lower fidelity images) may be employed in generating the intermediate images. Input images may be generated using one or more techniques described in U.S. Published Patent Application No. 2014/0016847, entitled "Multi-Phase Computed Tomography Image Reconstruction," filed Jul. 13, 2012, which is incorporated herein by reference in its entirety. For example, multiple image volumes may be reconstructed and intermediate image volumes, in time, are synthesized from the set of basis images. The Fourier slice theorem may be used as the basis of the image generation process from basis images. The method may include Fourier transforms, applications of specific masks in the Fourier domain, and inverse Fourier transforms. In this manner, multiple image volumes with smaller differences in time may be generated without additional back projection operations. The image syntheses may be performed on a slice-by-slice bases, without requiring reconstruction of all image slices. Further, additionally targeted image reconstruction may be performed directly via the synthesis method, which does not require compact support of the image object.

The intermediate image sets generated may then be used for the input for an image analysis algorithm to select a phase for final image reconstruction. The image analysis algorithm may leverage various aspects of motion characteristics to determine which aspects provide the most optimal phase in terms of vessel motion. In some embodiments, the algorithm (or algorithms) may utilize a cost function using some measure of motion, contrast, SNR, or the like to determine the phase or phases of least motion. Further, the cost-function may factor in conditions that are advantageous to subsequent coronary motion correction, such as gantry angle with respect to direction of vessel motion, to improve image quality. Further, the cost-function may also arbitrate between in-plane or through-plane vessels of the heart depending on the clinical use case of the final images. As one example, if stent follow-up studies are being performed on a proximal RCA (right coronary artery), the cost-function may provide added emphasis on through-plane vessel metrics as opposed to in-plane components. The cost-function may also entirely evaluate the myocardium characteristics instead of the vessels in a used case where perfusion studies are being done. An example framework for an auto phase detection algorithm is discussed in connection with FIGS. 12-31 herein.

Figure 7:
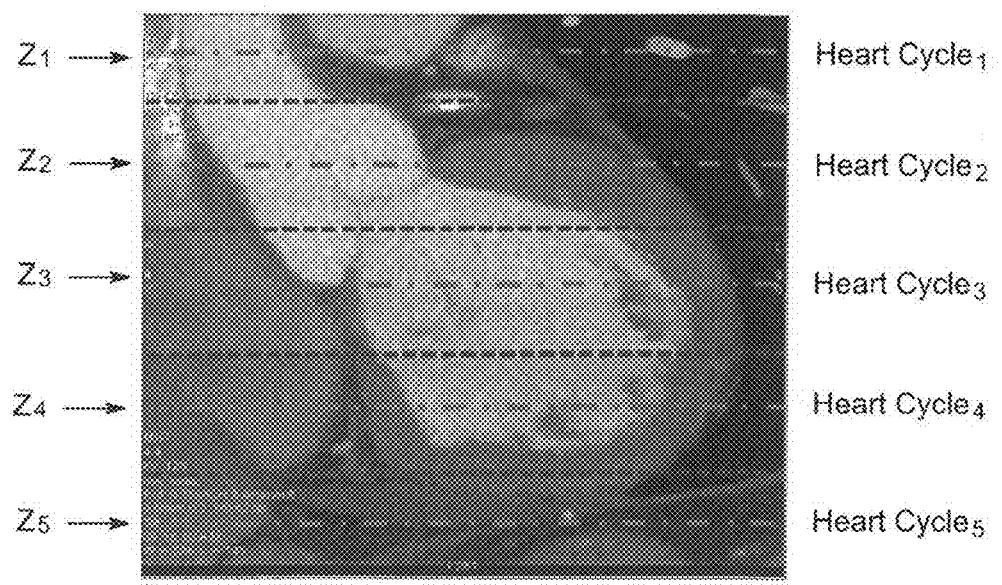
FIGS. 7 and 8 describe extensions of aspects of the presently disclosed subject matter to multi-heart cycle acquisitions in accordance with various embodiments.
Figure 8:
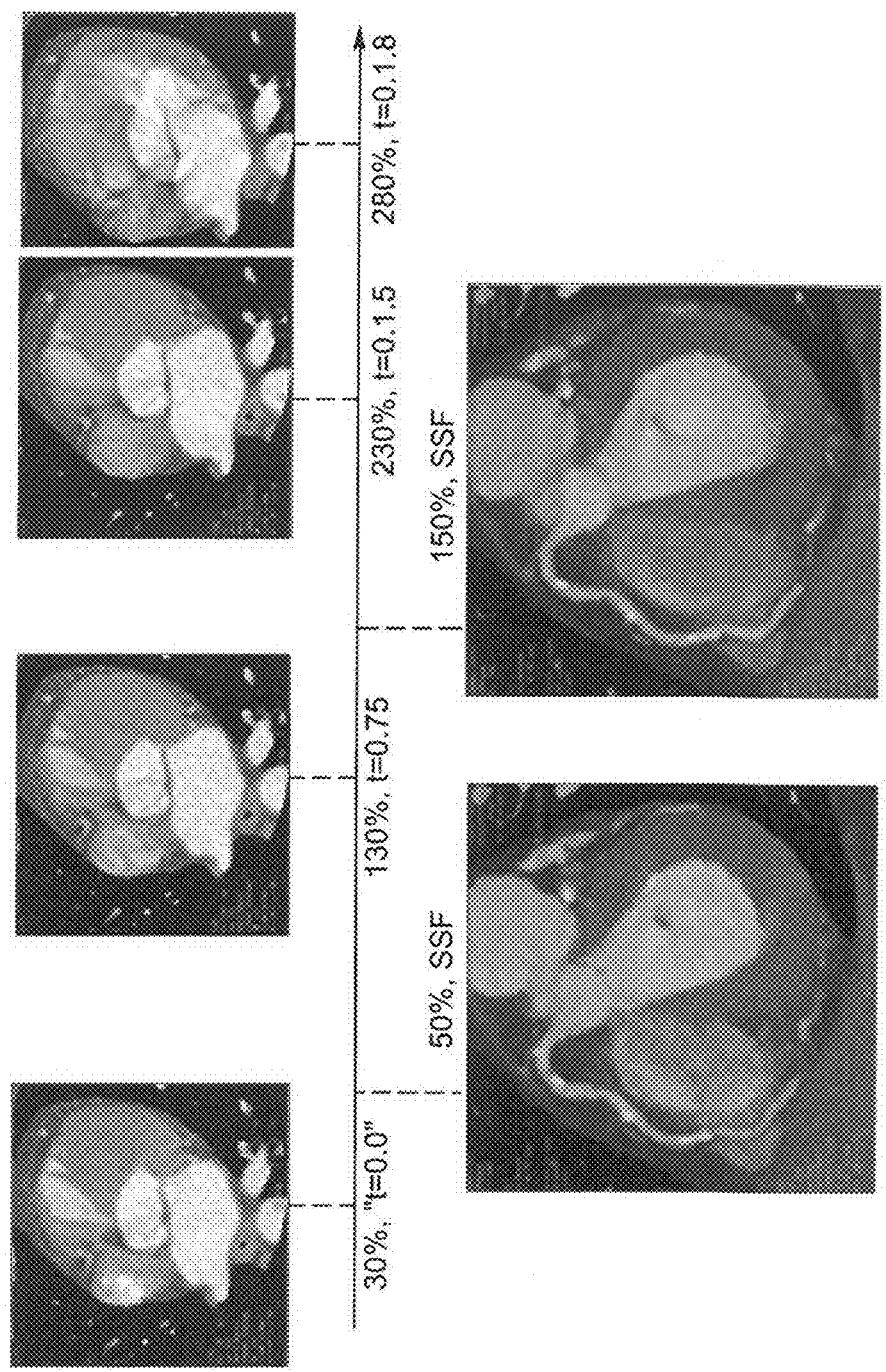

With reference to FIGS. 7 and 8, the phase selection may be extended to various multi-cycle acquisitions. The optimal phase selection may be extended to multi-beat acquisition, providing an optimized phase for each heart cycle in those acquisitions or, alternatively (e.g., given a clinical indications-based cost function), strike an appropriate balance between local (within each image slab or heart cycle) optimization and multiple beat/multiple slab global optimization. For example, a given phase location may be the best phase across all heart cycles as a whole but may not be the most optimal within a specific slab or heart cycle. Further, when multiple heart cycles are available for the same range of image locations (i.e., spatially), the autophase framework figure of merit (e.g., the selected or optimal phase) may also utilize additional factors besides degree, amount, or effect of motion, such as level of vessel contrast, to select the best phase and heart cycle to maximize or improve IQ for the resultant image volume. FIG. 8 illustrates an example of contrast timing over 2.5 beats. In the example of FIG. 8, for example, the 50% phase location within the first two heart cycles have comparable, minimal motion; however, the second heart cycle has better contrast opacification within the vessel compared to the surrounding region. Accordingly, the location from the second heart beat (150%) may be selected.

With continued reference to FIG. 2, the motion correction component 230 may correspond to (e.g., be performed by or otherwise associated with) the motion correction module 126 of the processing unit 120 in some embodiments. The motion correction component 230 may relate to motion correction or other post-processing of images in various embodiments. For example, the motion correction component 230 may provide a full fidelity reconstruction, and may adaptively apply motion correction and/or registration to reconstruct images for the selected phase (or phases). In various embodiments, a motion metric threshold may be evaluated to determine if motion correction is performed or not, and/or a slab coherency (and/or vessel registration) metric threshold may be evaluated to determine if registration techniques are applied.

Figure 9:
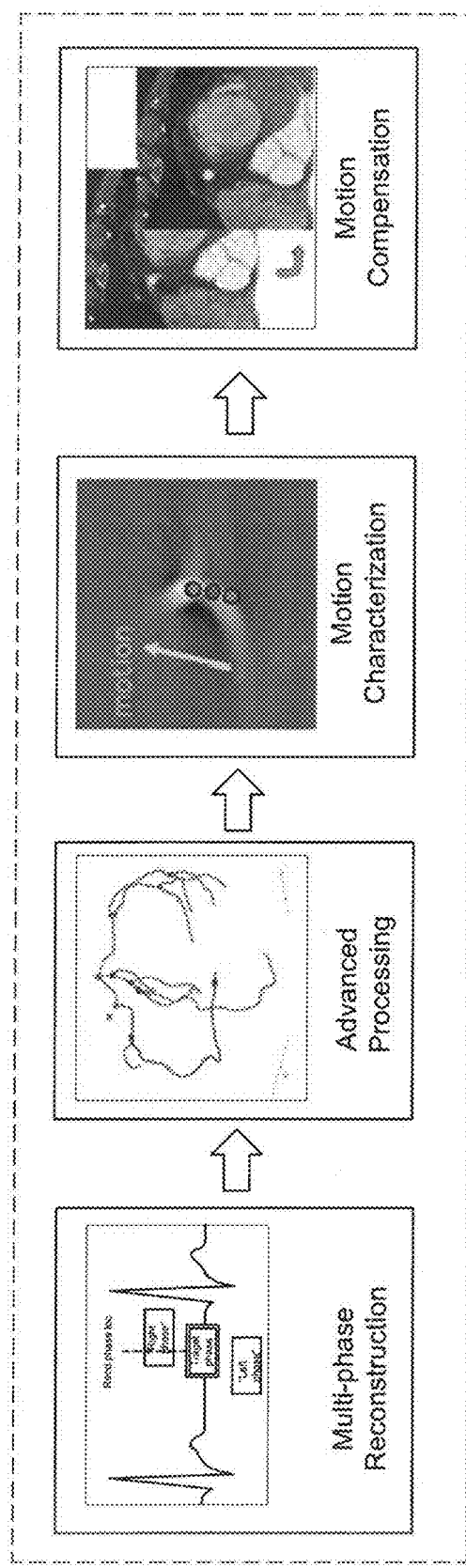
FIG. 9 describes various aspects of a motion correction or post processing component in accordance with various embodiments.
Figure 10:
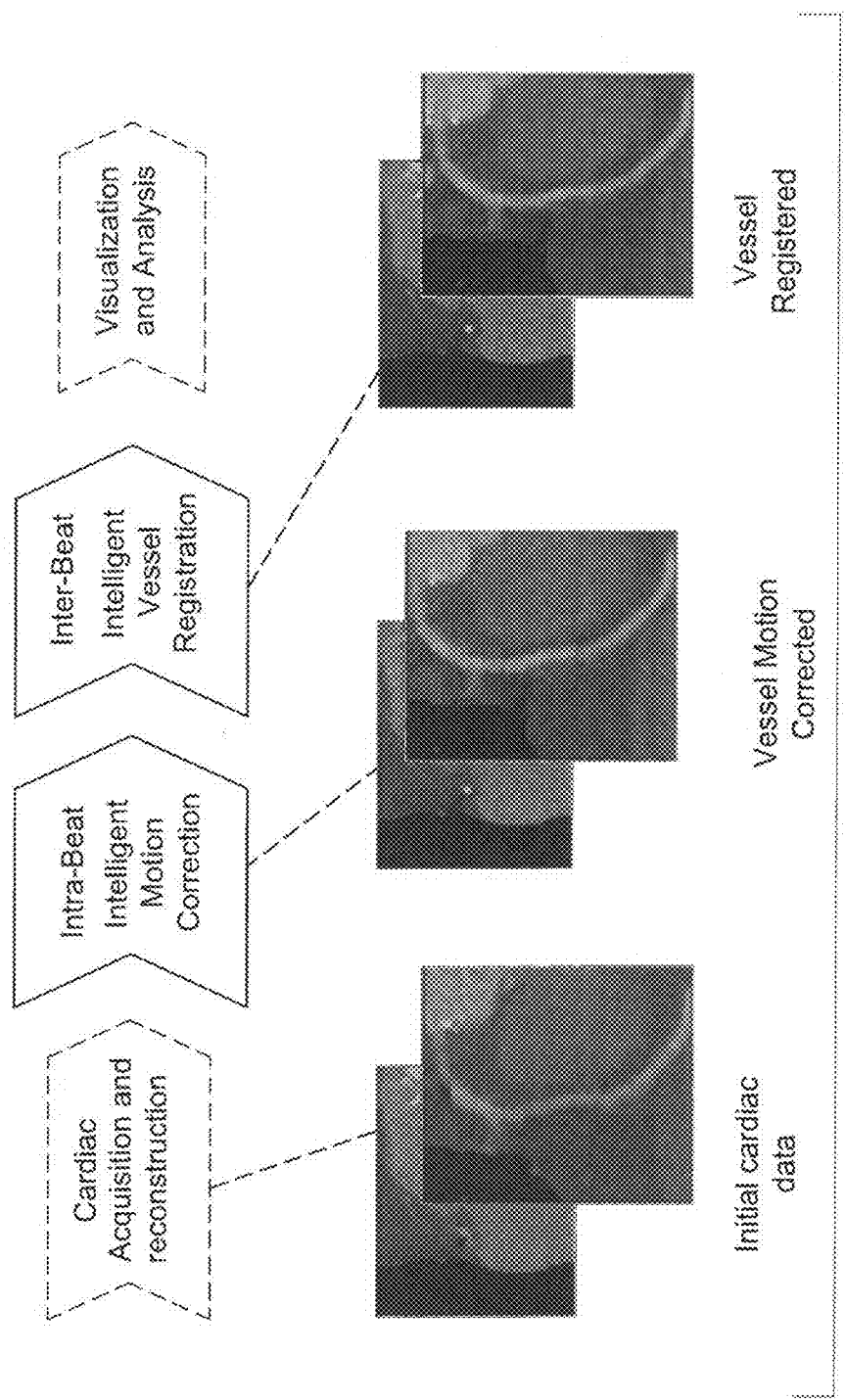
FIG. 10 describes various aspects of intelligent boundary and vessel registration (IBR) in accordance with various embodiments.

FIGS. 9 and 10 describe various aspects of motion correction for example embodiments. Generally, once an optimal phase is determined (e.g., via the retrospective component 220), a full fidelity image reconstruction (or reconstructions) for that phase may be automatically initiated, and final images for the optimal phase may be made available (e.g., via a display) for a practitioner (e.g., radiologist) to review. When the selected phase still has a significant amount of residual motion (e.g., as determined based on an appropriate motion metric), coronary motion correction may be adaptively applied to images, for example, by generating all necessary data for motion correction automatically prior to assessment by the practitioner. For example, if the selected phase is determined to have a low likelihood of requiring motion correction (e.g., based on a metric used to rank through-plane images, such as circularity and/or edge strength as discussed herein), then motion correction information may not be generated automatically prior to assessment by the practitioner. However, if the selected phase is determined to have a higher likelihood of requiring motion correction, then motion correction information may be generated automatically prior to assessment by the practitioner.

Similarly, for multi-beat acquisitions, if the resulting image volume still has a significant amount of slab-to-slab image misalignment as determined by the task-based cost function with the appropriate metric and threshold, automated boundary registration may also be adaptively applied. Accordingly, a workflow may be further improved, as a practitioner will not be required to determine at exam read time if it is needed to go back to apply motion correction steps and/or perform motion correction steps manually. FIGS. 9 and 10 generally describe various aspects of the motion correction component 230 in various embodiments.

Additionally, in various embodiments, a user may be allowed to prescribe an anatomy/vessel segment specific reconstruction request after an initial image review (e.g., at a workstation). For example, a practitioner may review images generated by default from a console, and find suboptimal images in some segment of the vessels. The practitioner may then send back a request to generate the best phase images for that anatomy, with the practitioner provided the opportunity to identify the range of locations needed for the new images. The mechanism may be able to start from the retrospective component 220 by generating intermediate images at available phases and within the user-selected anatomical range. Those generated intermediate images may then be input to an analysis algorithm (or algorithms) to select a best phase image or image series based on the practitioner's identified anatomy.

Figure 11:
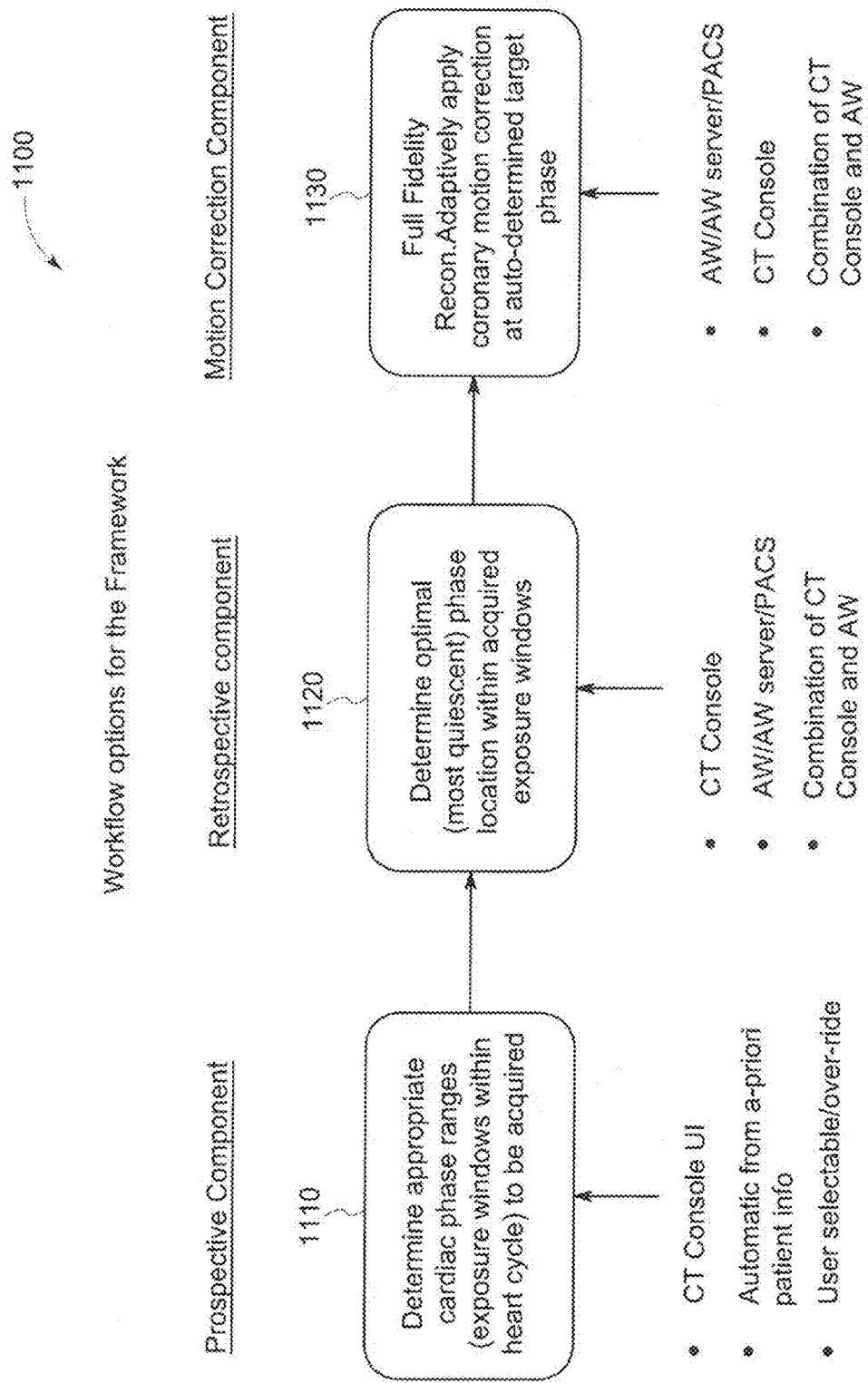
FIG. 11 describes various aspects of workflow options in accordance with various embodiments.

With reference to FIG. 11, it may be noted that various embodiments provide for improved workflow for example, for coronary imaging. The example framework 1100 depicted in FIG. 11 includes a prospective component 1110, a retrospective component 1120, and a motion correction component 1130. The prospective component 1110, retrospective component 1120, and motion correction component 1130 may be generally similar in certain respects to the corresponding components discussed in connection with FIG. 2. Various embodiments utilizing a framework such as framework 1100 provide for improved image quality and reduced time (e.g., reduced time and effort for selecting an optimal phase). Various steps or aspects of the components may be performed using one or more different aspects (e.g., physical portions or entities) of a system. For example, the prospective aspects (or a portion thereof) may be performed on a CT console. As another example, the cost function operation steps may be performed on one or more of a CT console, an image generation subsystem, or an image processing Workstation (AW or PACS). For example, intermediate information or images may be transferred between a CT console and image processing workstation. As one more example, the post-processing (e.g., motion correction or boundary registration) steps may be performed on a CT console, at a workstation, or a combination thereof.

Turning to FIGS. 12-31, various aspects relating to example algorithms for selecting an optimal phase for image reconstruction will now be discussed. It may be noted that cardiac motion may blur the coronary arteries in coronary CT angiography (CCTA) images, making it difficult for clinicians to perform an accurate diagnostic interpretation. Reconstructing the volume at the phase of the cardiac cycle with the least motion (or having the least noticeable effects of motion) provides cardiologists with a more accurate representation of the coronaries. However, generating images at a multitude of cardiac phases and evaluating each of them to find the optimal phase creates a workflow problem for clinicians in today's busy hospitals. Various embodiments discussed herein provide a fully automated algorithm that may be used a best (e.g., optimal, ideal, or preferred) phase for use in conjunction with image interpretation.

Conventionally, several approaches may be used to detect the best phase for CCTA reconstruction. Such approaches may quantify a metric of cardiac motion and choose the time of minimal motion as the best phase for reconstruction. For example, the kymogram approach calculates the motion of the center-of-mass of the heart from raw image data, replacing the ECG as a synchronization signal. Since this approach does not require image reconstruction, it is computationally efficient. However, a large difference (e.g., 12.5%) may be seen between manually and automatically chosen reconstruction phases under such an approach. Another approach uses the difference between low-resolution heart volumes at consecutive phases to estimate the motion of the heart. Because consecutive phases only differ by a few projections of data, motion will only be detected perpendicular to these projections, which causes the metric of heart motion to be coupled with motion direction. Also, the image quality of the coronary arteries has been estimated and optimized for motion correction based on entropy and positivity as well. However, such an approach requires a full segmentation of the coronary arteries. In contrast, various embodiments discussed herein provide an algorithm, technique, or approach that selects or determines the best phase based on one or more image quality metrics of intermediate information, which may be evaluated for one or more phases of a predetermined range. For example, in some embodiments a best phase is determined by calculating the image quality of through-plane vessels directly and pairing this with a binary metric that determines if image quality of in-plane vessels is acceptable, avoiding the dependency on motion direction seen in the phase difference approach. Further, by selecting the phase based directly on image quality, any inconsistencies between the levels of motion and image quality may be avoided or reduced.

Figure 12:
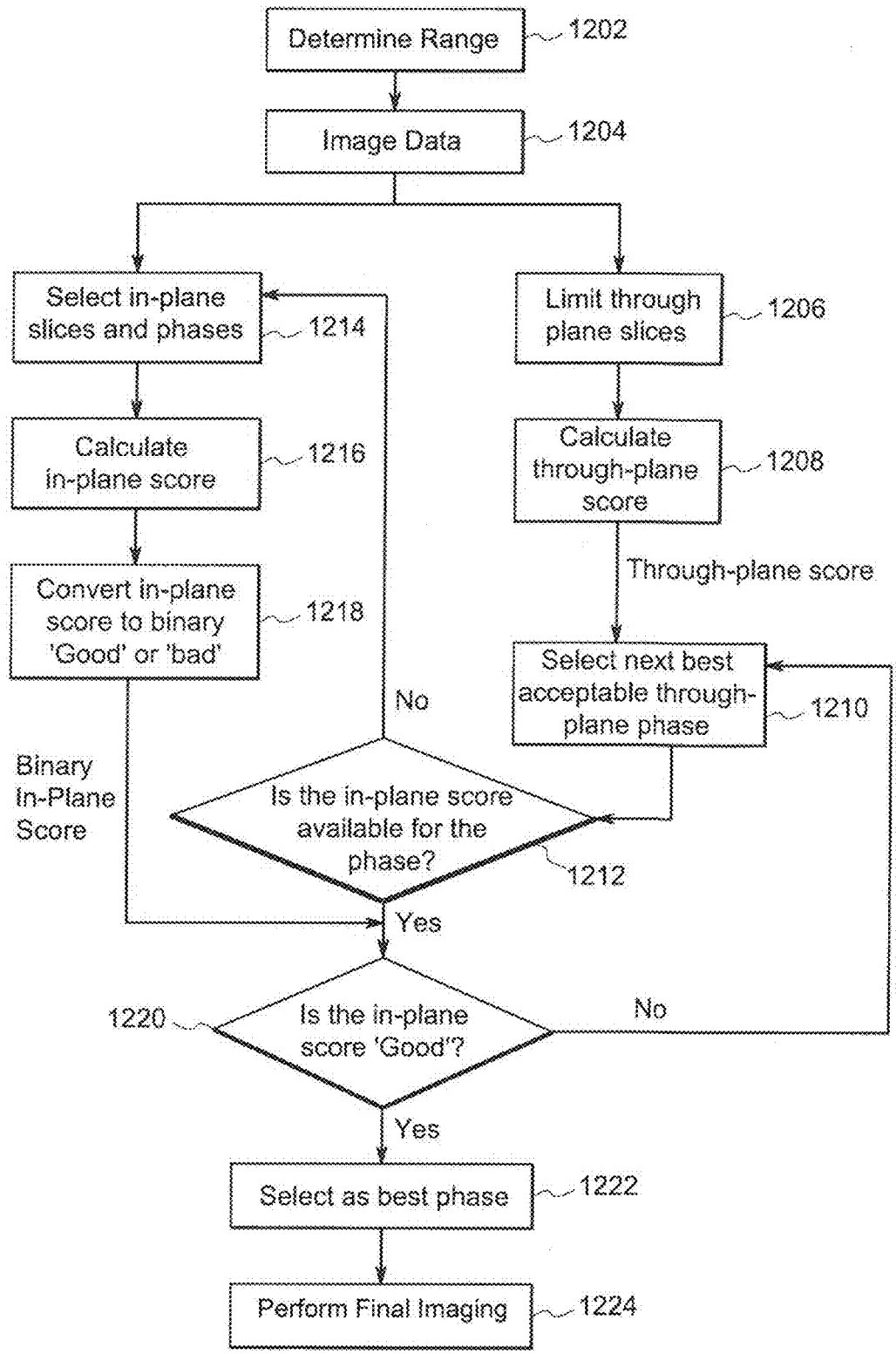
FIG. 12 illustrates a flowchart of a method for selecting a phase in accordance with various embodiments.

FIG. 12 provides a flowchart of an example method in accordance with various embodiments. The method 1200, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1200 may be able to be used as one or more algorithms to direct hardware to perform one or more operations described herein.

Various embodiments utilize both an IQ metric for through-plane vessels and an IQ metric for in-plane vessels to select the best phase. Generally, an intermediate image for each of the phases of the determined range (or ranges) is generated and scored based on one or more IQ metrics for through-plane vessels. (A through-plane vessel may be understood as a vessel or portion thereof that extends generally perpendicular to an image plane (e.g., within 45 degrees of perpendicular). An in-plane vessel may be understood as a vessel or portion thereof having a length that extends along the image plane within a slab thickness of the image (e.g., within a slab thickness of 12.5 millimeters. The phases are then ranked according to the through-plane score, and the phase having a highest through-plane score while still satisfying a threshold for an in-plane metric is selected as the best phase. The particular scoring values or parameters may vary in different embodiments. Further, alternate combinations of in-plane and through-plane scores may be used to select a best phase in alternate embodiments. For example, a weighting function may be employed additionally or alternatively to use of an in-plane acceptability metric. Further, in some embodiments, the in-plane phases may be evaluated as a whole, and if the in-plane phases do not satisfy a reliability threshold (e.g., if more than half of the phases do contain an identifiable in-plane vessel), the in-plane scores may be disregarded, and the phase having the best through-plane score may be selected.

In the example embodiment depicted in FIG. 12, the depicted algorithm utilizes two independent metrics that quantify image quality (IQ) for through-plane and in-plane vessels. The through-plane metric quantifies IQ for vessels travelling longitudinally through the volume. Generally, the through-plane metric may be more reliable, and thus weighted more heavily or given greater consideration, because the vessel shape is assumed to be circular in axial slices of the heart. The candidate best phase based on the through-plane metric is checked with the in-plane metric to ensure that in-plane vessel IQ is acceptable. The in-plane metric is calculated for several phases near the candidate phase and converted to a binary score of 'Acceptable' or 'Unacceptable'. In some embodiments, if in-plane vessels cannot be found in at least half of the investigated phases, results for in-plane vessels may be considered unreliable, and the candidate through-plane phase having the best through-plane image quality metric (or metrics) is accepted as the best phase. Otherwise, the candidate phase may be accepted only if the in-plane vessels meet an adjustable acceptability threshold. The acceptability threshold may be lowered, for example, if motion correction will be applied after reconstructing the chosen phase. If the first candidate phase is not accepted, the phase with the next best through-plane IQ may be selected for analysis of the corresponding in-plane acceptability, and the in-plane check is repeated. The in-plane threshold may also be modified adaptively based on the combination of through-plane and in-plane image quality. For example, in one example scenario, when the next best through-plane score is below 75% of the maximum score (e.g., the best through-plane score) and no phase has yielded 'Acceptable' in-plane vessels, the acceptability threshold of in-plane vessels may be decreased. The in-plane check may then be repeated restarting with the best through-plane phase. Calculations may repeat in this manner until a phase is found with a high through-plane score and acceptable in-plane vessels.

In the illustrated embodiment, at 1202 a range or ranges of phases for evaluation are determined, for example using a prospective component as discussed herein (e.g., prospective component 210, prospective component 1110). At 1204, image data is generated. For example, a CT acquisition unit may be operated to obtain imaging data over the range or ranges determined or selected at 1202, and intermediate images generated for each phase over the range.

At 1206, in some embodiments, the number of through-plane slices may be limited, for example, to reduce computational requirements. For example, any slices not having a through-plane vessel may be excluded. At 1208 of the illustrated embodiment, a through-plane score is calculated for each phase of the selected range or ranges. The score may be based, for example, on circularity, edge strength, or a combination thereof. The various phases may then be ranked, highest to lowest, by through-plane score (with the highest through-plane score assigned to the phase having the best through-plane metric). At 1210, the phase having the highest through-plane score is selected for further evaluation.

At 1212, it is determined if an in-plane score for the phase selected at 1210 is available or has already been determined. If an in-plane score is available, the method proceeds to 1220; however, if an in-plane score for the phase selected at 1210 is not available, the method proceeds to 1214. At 1214, in-plane phases and slices are selected. Generally, at least the phase selected at 1210 is selected. Additional phases (e.g., phases near the selected phase) may also be selected for evaluation at 1214. All or a portion of the slices for a given phase (or phases) may be selected. Limiting the number of slices selected in various embodiments may reduce computational time and/or computational requirements. For example, slices not having an in-plane vessel may be excluded. At 1216, an in-plane score is calculated for the phase or phases selected at 1214. The score may be based, for example, on an IQ metric corresponding to edge strength. At 1218, the in-plane score is converted to a binary score (e.g., "good" or "bad," "acceptable" or "unacceptable"). The conversion may be based on a threshold. The threshold may be adjusted in some embodiments. For example, if a low percentage of phases satisfy the threshold, the threshold may be reduced.

At 1220, it is determined if the in-plane score for the phase selected at 1210 is "good" or satisfies the in-plane threshold. If the in-plane score is sufficient to satisfy the threshold, the phase selected at 1210 is selected as the phase for final imaging at 1222, and the method proceed to 1224 for final imaging (e.g., reconstruction, and, in some embodiments, motion correction). If the in-plane score for the phase selected at 1210 is not satisfactory, the method returns to 1210, the previously selected phase is removed from consideration, and the remaining phase having the highest through-plane score is selected. It may be noted that other approaches or techniques may be employed in various embodiments. As just one example, instead of a binary in-plane score being utilized as shown in FIG. 12, weighted combinations of in-plane and through-plane scores may be utilized to select a best phase.

Figure 13:
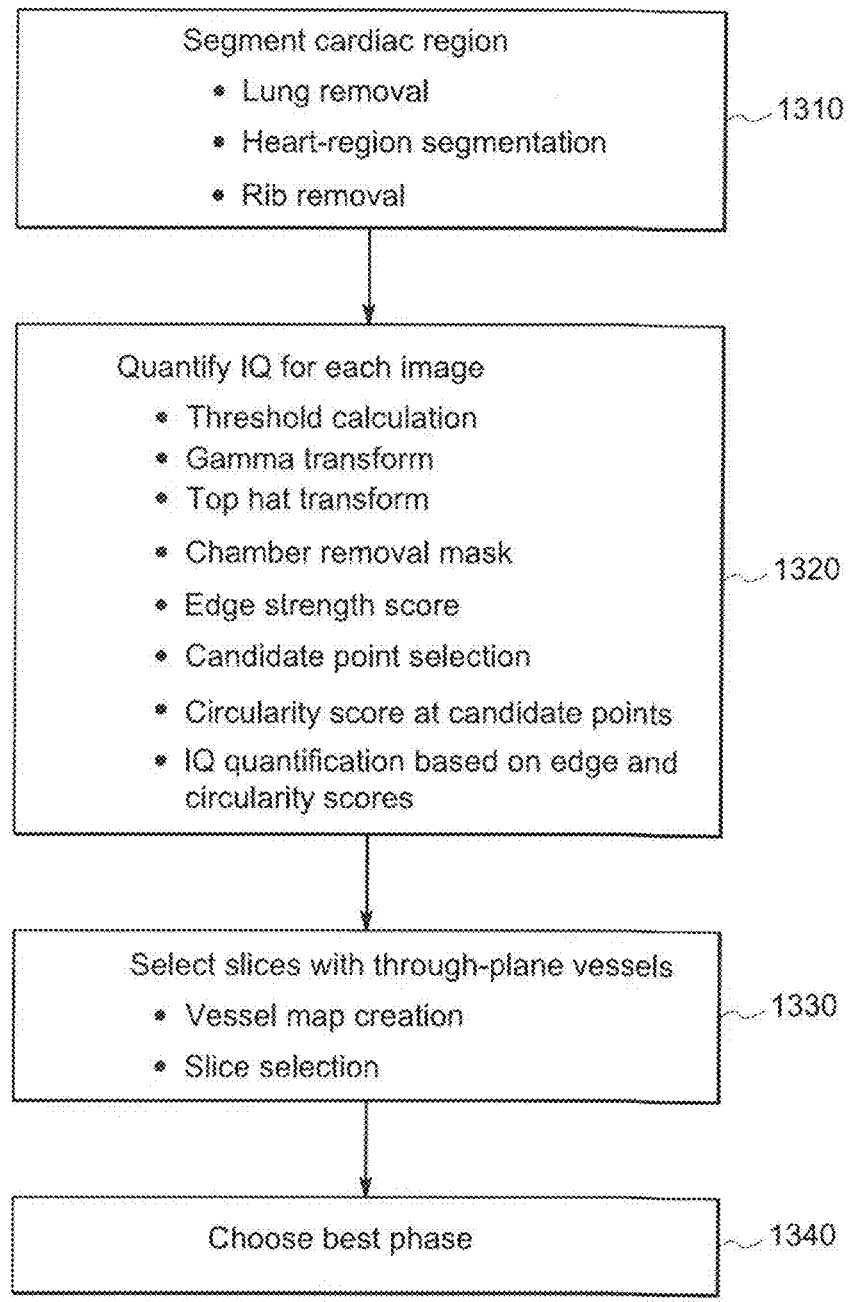
FIG. 13 illustrates a flowchart of a method for determining through-plane scores in accordance with various embodiments.

The determination of a through-plane score in various embodiments will next be discussed in greater detail, with particular reference to FIG. 13. In the illustrated embodiment, CT images reconstructed from a number of phases in the cardiac cycle and a number of slices from the CT exam are input to the through-plane metric. IQ is calculated in the right and left sides of each image based on region edge strength and circularity. Slices that do not contain through-plane vessels may be excluded. For each phase, the IQ metric of all slices are summed. In the illustrated embodiment, the best phase occurs when the sum of the IQ metrics is the highest. An example summary of the steps to calculate the through-plane score is shown in FIG. 13.

In the first block 1310, a cardiac region is segmented. Since the algorithm does not assume a full 3D dataset for the illustrated embodiment, standard segmentation algorithms for the heart may not be appropriate for use with the illustrated embodiment. A segmentation algorithm for axial slices of the heart may be employed as follows. First, an initial segmentation is performed to remove the lungs and spine. The location of the ribs are then determined once per slice and removed for images at all phases for the slice. The steps for segmentation for an example embodiment are summarized in FIGS. 14A-G.

The lungs may identified by applying a threshold at 550 Houndsfield Units (HU) to the image, where regions of low CT number are identified as potential lung regions. In the illustrated embodiment, regions above the threshold are labeled with a connected-components algorithm using 4-connectivity, and the region with the most pixels is selected. A morphological closing is performed on the region because shading can cause values within the cardiac region to fall below the threshold. This completes segmentation of the lungs. (See FIG. 14B.)

Next, the heart region may be segmented. The Euclidian distance, D, from any point on the image to the closest point on the lungs is calculated. The region with distance above a threshold, $D_{Thresh}$, is identified as the center of the heart (see FIG. 14c). $D_{Thresh}$ is defined as the product of the maximum distance and a scaling factor α. If α is too large, the shape of the heart may not be preserved, while too small an α may cause parts of the ribs and spine to be included in the heart region. In the example algorithm implementation α=0.8, and D and $D_{Thresh}$ may be provided by the following:

$$D=\sqrt{(x_1-x_2)^2+(y_1-y_2)^2}$$

$$D_{Thresh}=\alpha*\max(D)$$

The initial heart segmentation may include all values not in the lungs that are within a Euclidian distance of $D_{Thresh}*$ (1+β) from the central heart region. This removes any regions that branch off of the center of the heart where β is the tolerance for branching regions. Too large a β will include large parts of the ribs and spine while too small a β will remove outer edges of the heart. In the example algorithm implementation, β=0.15.

Figure 14A:
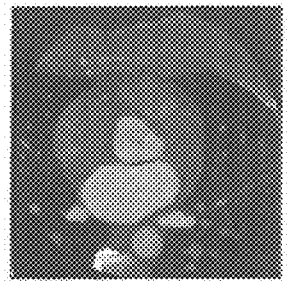
FIGS. 14A-G illustrates steps in a segmentation process in accordance with various embodiments.
Figure 14B:
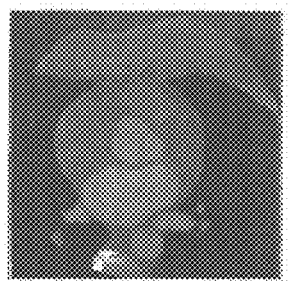
Figure 14C:
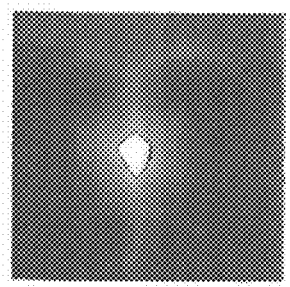
Figure 14D:
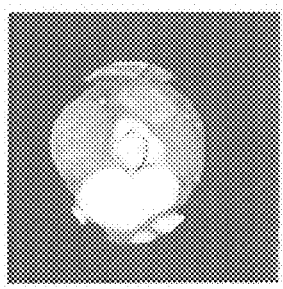
Figure 14E:
Figure 14F:
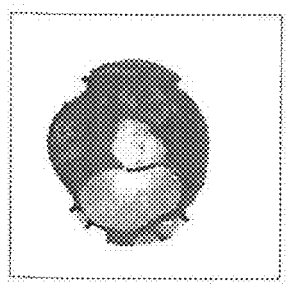
Figure 14G:

Next, the ribs may be removed. In the example embodiment, the ribs are removed by finding points on the right and left side of the heart where the ribs connect to both the heart and lungs, hereafter referred to as rib connection points. This is only done once per slice because the ribs will be in the same location for each phase. The ribs are identified as regions in the top half of the image that were removed by the initial heart segmentation, are not a part of the lungs, and intersect both the initial segmented region and the edge of the field of view. The lowest and most central points on this region are identified for the right and left side of the image and labeled as the rib connection points (see. FIG. 14E). If no appropriate points can be found, the ribs are understood as not present and the segmentation is complete.

Otherwise, a line is automatically drawn between the rib connection points and all points above it are removed. Generally, this line should not go through bone or the center of the heart. Furthermore, the line should avoid passing through any chambers of the heart if possible. In the illustrated embodiment, this logic is implemented by drawing the line as a in path (see FIG. 14F). The initial cost for each pixel in the heart region is equal to the reconstructed CT number. This gives additional cost when passing through chambers of the heart. Points outside the initial heart segmentation are not considered as possible paths for the line. Values above 1300 are not considered as possible paths for the line to assure that the path does not travel through bone. To discourage the path flow going through the center of the heart, an image is constructed whose value is equal to 700 in the heart center, defined previously as the region where $D>D_{Thresh}$, and decreases linearly to zero at the pixel that halfway between the center of the heart and the lungs. A maximum value of 7th) is chosen to allow no greater than a 100% increase in cost, assuming soft tissue values ≥700. This image is added to the previously defined cost image. The cost weighted distance is calculated for each rib connection point using a geodesic time algorithm, where the distance between points $(x_1,y_1)$ and $(x_2,y_2)$ is calculated using quasi-Euclidian distance, a piecewise variation of Euclidian distance:

Quasi-*Euclidian* Distance =

$$\begin{cases} |x_1-x_2|+(\sqrt{2}-1)|y_1-y_2| & \text{if } |x_1-x_2|>|y_1-y_2| \\ (\sqrt{2}-1)|x_1-x_2|+|y_1-y_2| & \text{otherwise} \end{cases}$$

The two cost weighted distance functions are summed and the minimum cost path is selected as the pixel with the smallest value for each column between rib connection points. The final segmentation is achieved by including the region below this path and performing a morphological open to smooth the edges of the segmentation. (See FIG. 14G.)

Figure 15A:
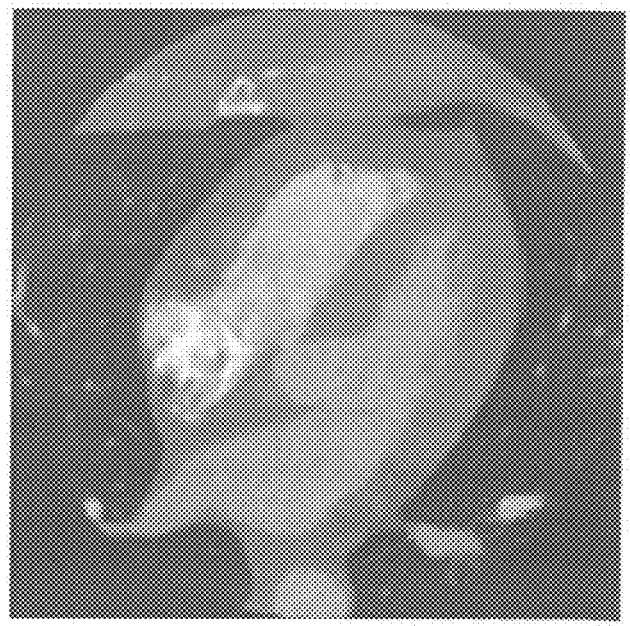
FIG. 15A illustrates an example image and FIG. 15B illustrates an example histogram used in conjunction with segmentation in various embodiments.
Figure 15B:
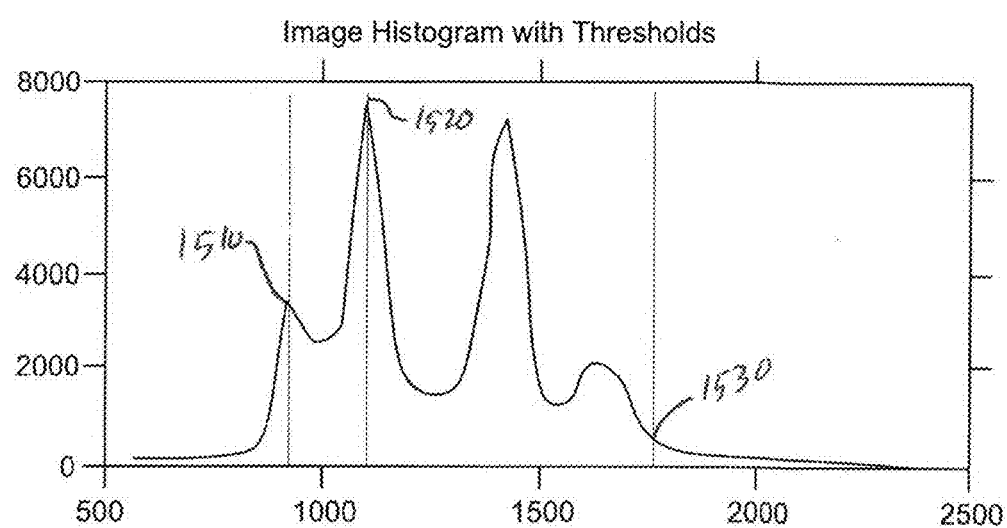

Returning to FIG. 13, in the second block 1320, an IQ for each image is quantified. First, thresholds may be calculated. Once per slice, three thresholds may be calculated: a soft tissue threshold, a contrast threshold, and a maximum value threshold. In the example embodiment, each threshold is calculated using the segmented image histogram divided into bins with a width of 30 HU. The soft tissue threshold is the approximate value of the background tissue in the heart. It is calculated as the first peak in the segmented image histogram. The contrast threshold is the approximate value in the chambers of the heart. It is calculated as the second peak in the histogram (after the soft tissue threshold). The maximum value threshold is the largest value in the image that does not include contrast pooling or calcification. It is found by the highest histogram bin that contains at least 0.05% of the total image points. An example of each of these thresholds may be seen in FIGS. 15A-B. (FIG. 15A depicts an original image and FIG. 15B depicts an example image histogram with three thresholds—a soft tissue threshold 1510, a contrast threshold 1520, and a maximum value threshold 1530.) The soft tissue and contrast thresholds may be used to create a chamber removal mask while the maximum value threshold may be used to calculate a top hat image.

Next, a gamma transform may be performed. Very high values in the image, often due to calcification or contrast swirling, may overpower the results of gradient and filtering operations used to calculate the edge strength score. A gamma transform is performed on the values above the maximum value threshold (MVT) in each image to mitigate this effect. The gamma transform may be expressed as:

$$\begin{cases} MVT+(x-MVT)^\gamma & \text{if } x>MVT \\ x & \text{otherwise} \end{cases}$$

Lower γ values give more sudden thresholds, removing gradient information above the MVT, but better rejecting high values in the image. Values ranging from 0.5-0.8 provide similar results. In the example algorithm implementation γ=0.7.

Next, a top hat transform may be performed. Vessels may be identified as small high-valued regions in the image. A morphological top bat transform removes large, constant-valued structures from an image that is the output of a grayscale opening operation. The top hat transform, T(f), is applied to the gamma transformed image, f, with structuring element s where ∘ denotes the grayscale opening of the image:

$$T(f)=f-(f \circ s)$$

Figure 16A:
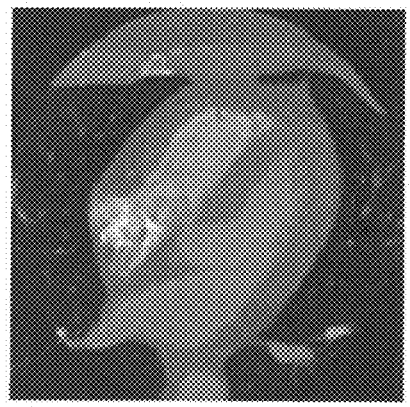
FIGS. 16A-C illustrate steps to image a top hat transform in accordance with various embodiments.
Figure 16B:
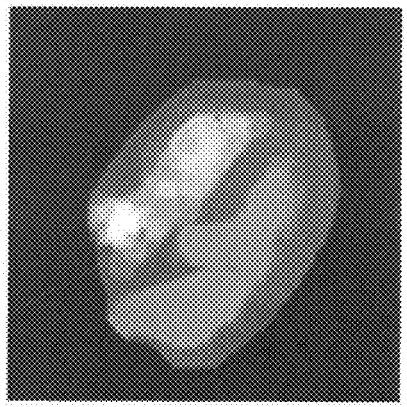
Figure 16C:
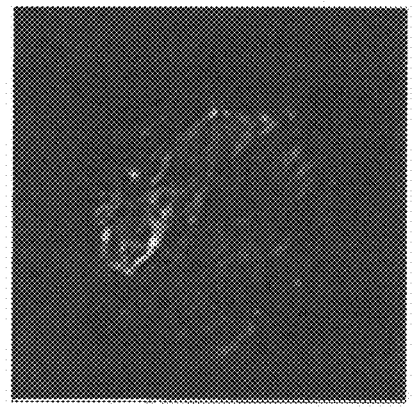

Grayscale opening operations consist of consecutive erosion and dilation operators, where erosion chooses the minimum value in the region of the structuring element and dilation chooses the maximum value. A 9×9 circular structuring element is used to remove through-plane vessels during the erosion operation. In the depicted example, regions outside the final heart segmentation are included in this operation only if their value is greater than the soft tissue threshold. This ensures that partially removed large structures do not appear to be small structures during the top hat transform. By subtracting the opened image from the original image, the top hat transform will include only high-valued details that are smaller than the structuring element. The image is resized to 128×128 for this operation then scaled back to 512×512 using bicubic interpolation for computational efficiency. An example of the top hat transform calculation is shown in FIGS. 16A-16C. (FIG. 16A illustrates an original image, FIG. 16 B illustrates a segmented grayscale morphological open, and FIG. 16C illustrates a segmented top hat transform.)

Next, a chamber removal mask may be created. Since through-plane vessels typically appear next to soft tissue, a chamber removal mask may be created to remove the chambers of the heart as well as any contrast swirling from the top hat image. The morphological open of the image will include large structures, making it a good indicator of heart chamber location. The first step in generating the chamber removal mask is to the transform the values of the morphologically opened image that is generated during the top hat transform. (See FIGS. 16B and 17B). The values are scaled so that the range from soft tissue threshold to contrast threshold in the open image is mapped to a range from one to zero. (See FIG. 17C.)

Figure 17A:
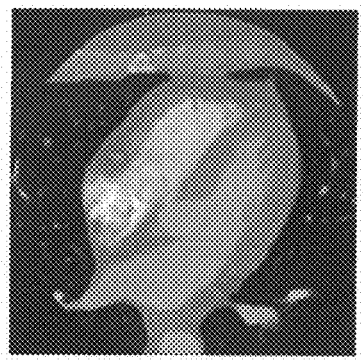
FIGS. 17A-F illustrate steps in chamber removal mask creation in accordance with various embodiments.
Figure 17B:
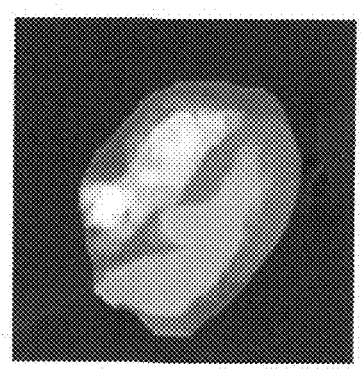
Figure 17C:
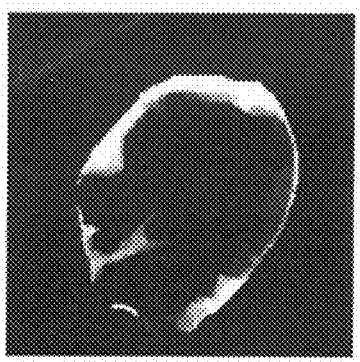
Figure 17D:
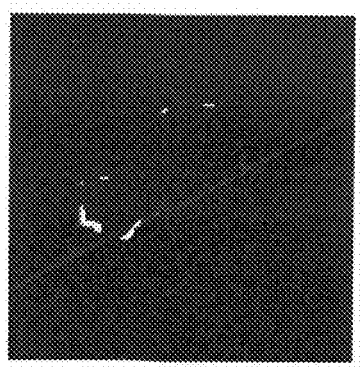
Figure 17E:
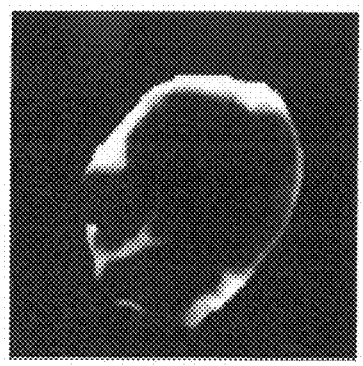
Figure 17F:
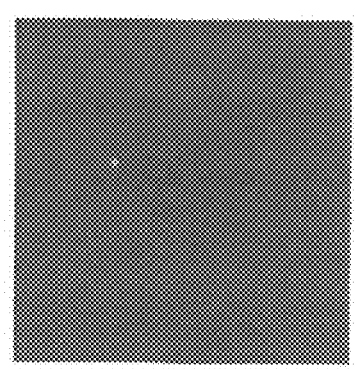

Contrast swirling may cause inconsistent values in the chamber that may appear as small structures during the opening operation. This is why the edges of the right atrium are still present in the mask in FIG. 17C. To account for this, any values connected to a chamber that are greater than the maximum value threshold are marked as regions of contrast swirling. Regions of contrast swirling are dilated and given a value of zero in the mask (see FIG. 17D). The initial mask is smoothed with a 12×12 averaging kernel to assure that the edges of the chambers are removed. Multiplying the top hat transform image by the final chamber removal mask (FIG. 17E) removes all heart chambers (FIG. 17F). The chamber removal mask is also used to calculate the edge strength score in the illustrated embodiment.

Figure 18A:
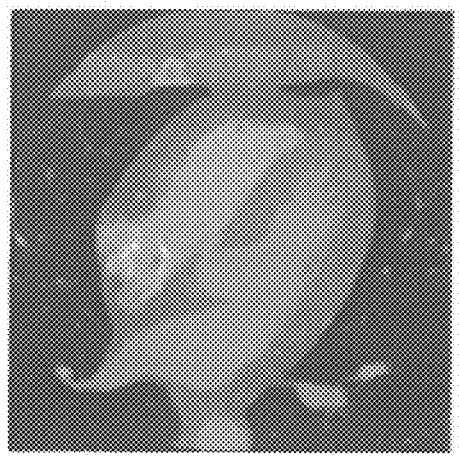
FIGS. 18A-D illustrate steps in edge score calculation in accordance with various embodiments.
Figure 18B:
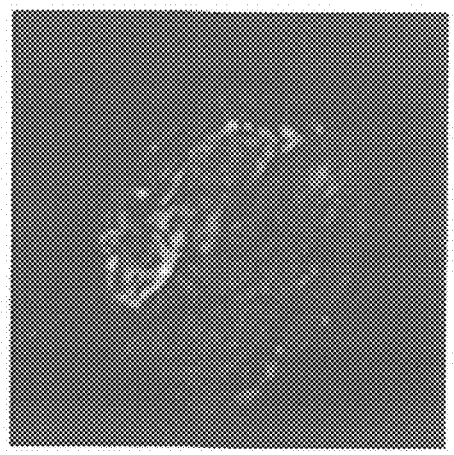
Figure 18C:
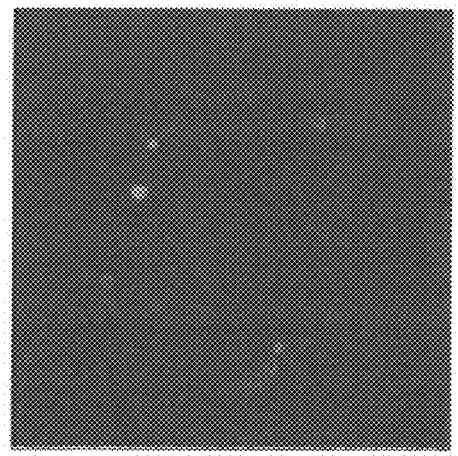
Figure 18D:
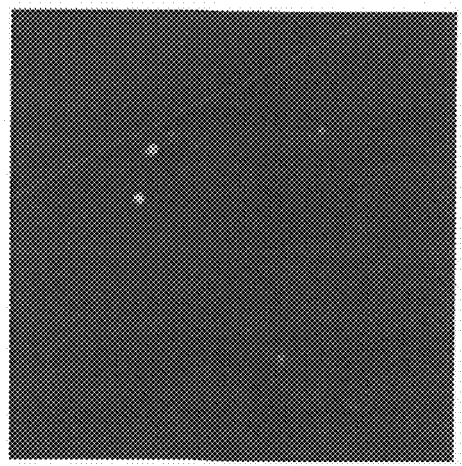
Figure 19A:
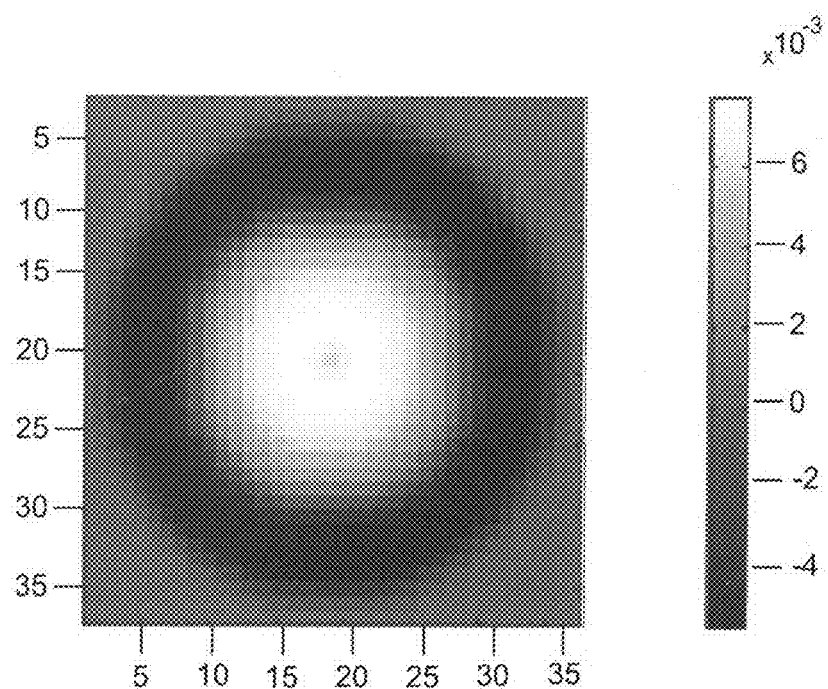
FIG. 19A-B illustrate aspects of a match filter in accordance with various embodiments.
Figure 19B:
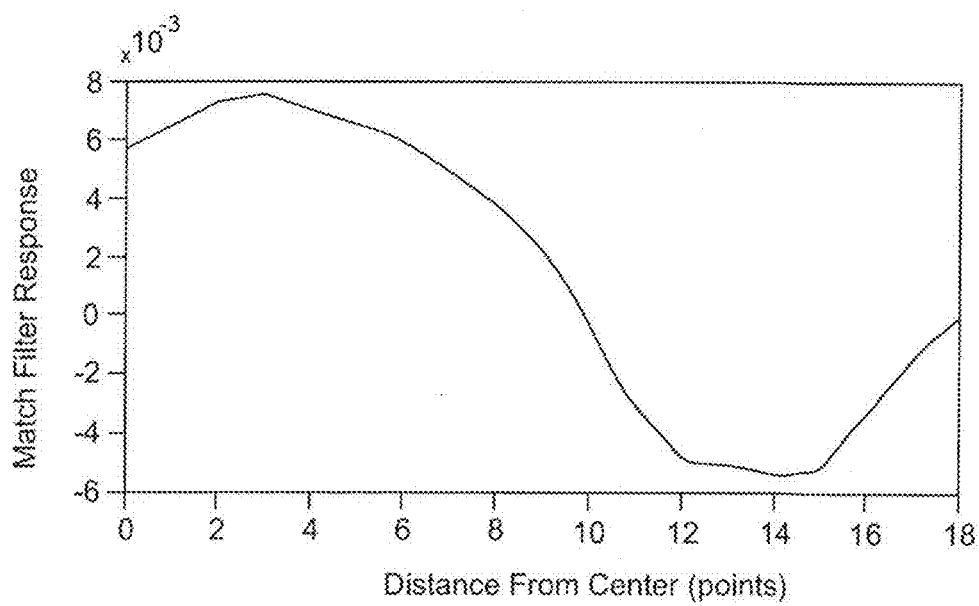

Next, an edge strength score is generated. In the illustrated embodiment, the edge strength score quantifies the strength and circularity of the top hat image gradient at all pixels. A summary of the process can be seen in FIGS. 18A-D. The gradient of the top hat transform is calculated using a Sobel filter and then multiplied by the chamber removal mask (FIG. 18C). Next, a match filter is applied that has a maximum response to circular disks in the gradient image. (FIG. 19A illustrates an example match filter and FIG. 19B illustrates an example graph of match filter value based on distance from the center of the filter). The match filter may be radially symmetric with a positive response to values within 10 pixels of the center. The gradients of vessels with a radius less than 10 pixels will be contained in the positive response of the match filter. The negative lobe of the filter from 10-18 pixels from the center elicits a weaker result from structures that are longer or larger than 20 pixels in any direction. The convolution of the match filter with the top hat image gradient gives the edge strength score at each point in the image.

Figure 20A:
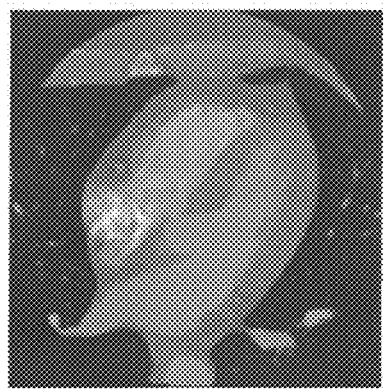
FIGS. 20A-D illustrate aspects of candidate point selection in accordance with various embodiments.
Figure 20B:
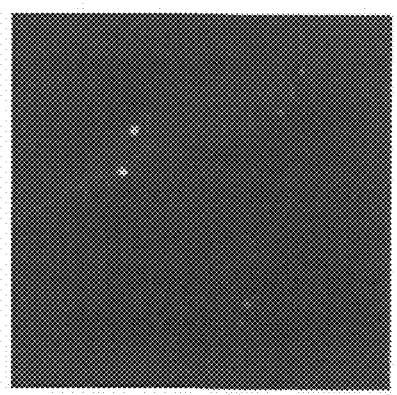
Figure 20C:
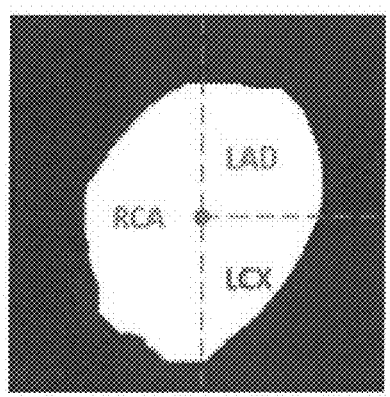
Figure 20D:
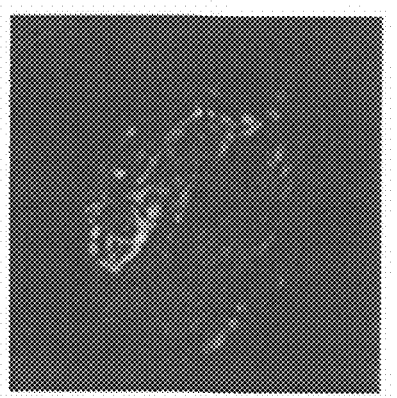

Next, a candidate point may be selected. In the illustrated embodiment, pixels with the highest edge strength scores are likely to be vessels. FIG. 20A illustrates an example original image and FIG. 20B illustrates an edge strength score for the image of FIG. 20A. It may be noted that the edge strength score will give a high response to any structure whose longest dimension is less than 20 pixels, even if it is not circular. Therefore, candidate points from each side of the heart with high edge strength scores are analyzed further to determine their circularity. For each image, a binary mask is created with pixels within the segmented cardiac region set equal to one. The centroid of the binary mask is considered as the center point that defines three regions of the heart (FIG. 20C): the right side containing the RCA, the left anterior quadrant containing the LAD, and the left posterior quadrant containing the LCX. Pixels that are greater than each of their eight neighbors are found in the edge strength image and identified as regional maxima. Candidate vessel center points are selected as the three highest valued regional maxima in each of the three regions (FIG. 20D).

Figure 21A:
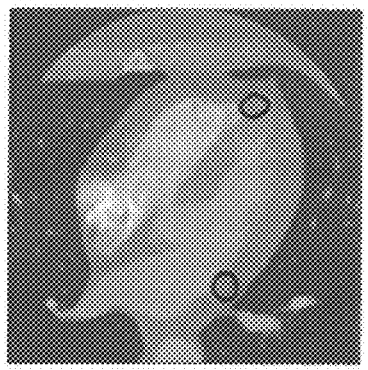
FIGS. 21A-E illustrate examples of circularity scoring in accordance with various embodiments.
Figure 21B:
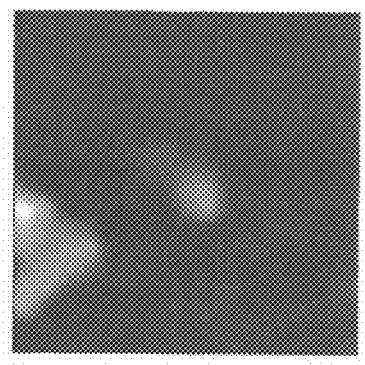
Figure 21C:
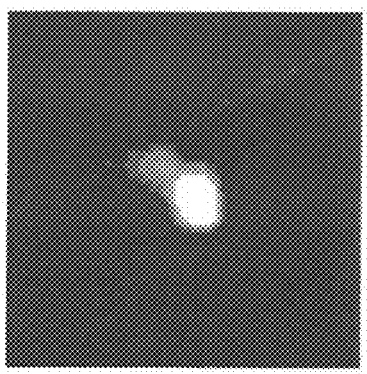
Figure 21D:
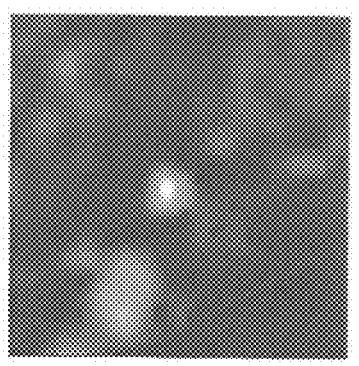
Figure 21E:
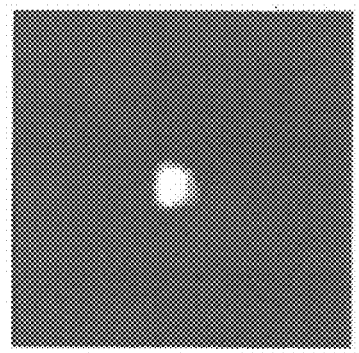

Next the circularity score may be calculated for each candidate point. (FIG. 21A illustrates an example original image with two candidate points circled, FIG. 21B illustrates a ROI in the top hat image near the LAD, FIG. 21C illustrates a threshold decomposition of the LAD region with an example circularity score of 0.518, FIG. 21D illustrates a ROI in the top hat image near the LCX, FIG. 21E illustrates a threshold decomposition of the LCX region with an example circularity score of 0.772.) The circularity score is a measure of compactness calculated for each candidate point. Previously, a measure of compactness has been proposed for a binary image, where a value of one is the most compact and higher values are less compact. The measure may be expressed as:

$$\text{Compactness} = \frac{\text{Perimeter}_d^2}{4\pi \text{Area}_d}$$

This compactness measure operates on a single region in a binary image. Therefore, the region of interest may be broken down into a series of binary images, and the vessel region is chosen. The circularity score is a weighted sum of compactness metrics for the vessel region in each binary image. A square 70×70 ROI around each candidate point in the top hat image is considered (FIG. 21B/D). First, the center of the vessel is identified as the largest value in a five pixel radius of the candidate point. Next, the ROI is thresholded into four levels: >50%, >40%, >30%, and >20% of the vessel center value. For each level, regions above the threshold are labeled with a connected-components algorithm using 4-connectivity, and the region that contains the center of the vessel is selected. The compactness of each of these four binary regions is calculated and compiled into a measure of circularity that may be expressed as:

$$\text{Circularity} = \frac{1}{\sum_{d=2}^{s} d} \sum_{d=2}^{s} d * [2 - \max(\text{Compactness}_d, 2)]$$

As used herein, compactness$_d$ refers to the compactness of the selected region when the ROI is thresholded at d*10% of the center vessel value. Values greater than two for the compactness are extremely poor circles that should not be considered. Therefore, compactness values are transformed so that the original range of one to two corresponds to one to zero. An increased weight is placed on higher thresholds because distortion seen at lower thresholds is lower in magnitude and, therefore, should have a lower effect on the circularity metric.

Figure 22:
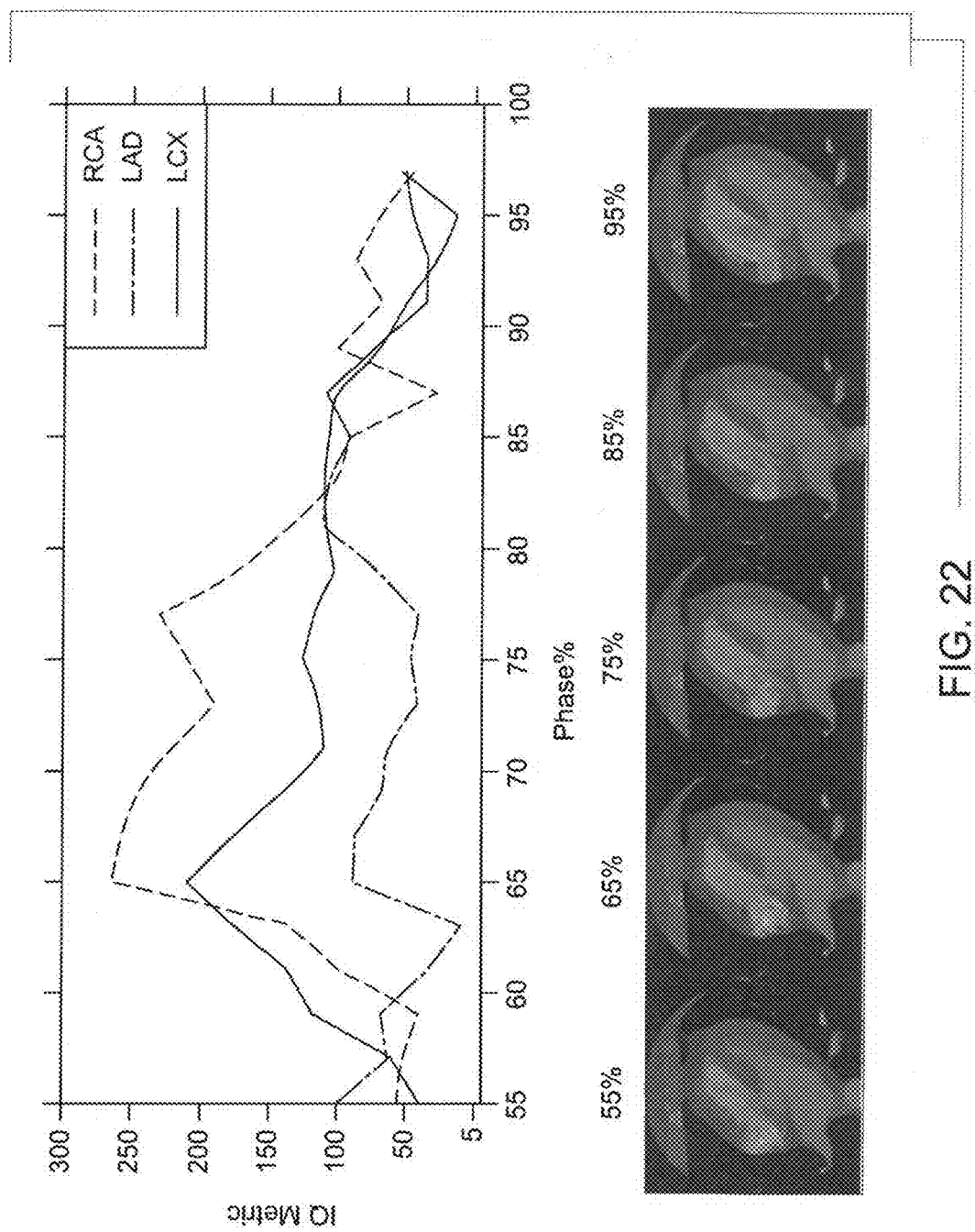
FIG. 22 illustrates examples of images and IQ metrics in accordance with various embodiments.

Next, IQ may be quantified, for example based on edge strength and circularity scores. In the depicted embodiment, after edge and circularity scores are calculated, they are multiplied together for each candidate point to determine the final IQ metric. This IQ metric has high values for regions with high edge gradient and high circularity. The IQ for the RCA, LAD, and LCX is the point with the highest IQ score in the associated vessel region (FIG. 20C). The IQ calculation is executed for each image in a slice. At this point, IQ for all input phases across a slice can be compared for each vessel, as seen in FIG. 22. (As used herein, the % identified with a given phase corresponds to the portion of an R-R cycle at which the phase is located temporally, with 0% corresponding to the beginning of the cycle, and 100% corresponding to the end of the cycle.)

Returning to FIG. 13, in the third block 1330, slices with through-plane vessels are selected. It may be noted that an intermediate image used to provide a through-plane score may be generated using slices that have through-plane vessels, or otherwise reducing the total number of slices processed and used to provide the through-plane score. Once IQ has been calculated for all slices, the results may be compiled to determine the best phase for the right side, the left side, and the best overall phase. In the illustrated embodiment, only IQ scores from slices that contain through-plane vessels are used to determine the best phase. The locations of the highest IQ point for each vessel region (one RCA, one LAD, one LCX), called potential vessel points, are considered to determine if a through-plane vessel is present.

Figure 23:
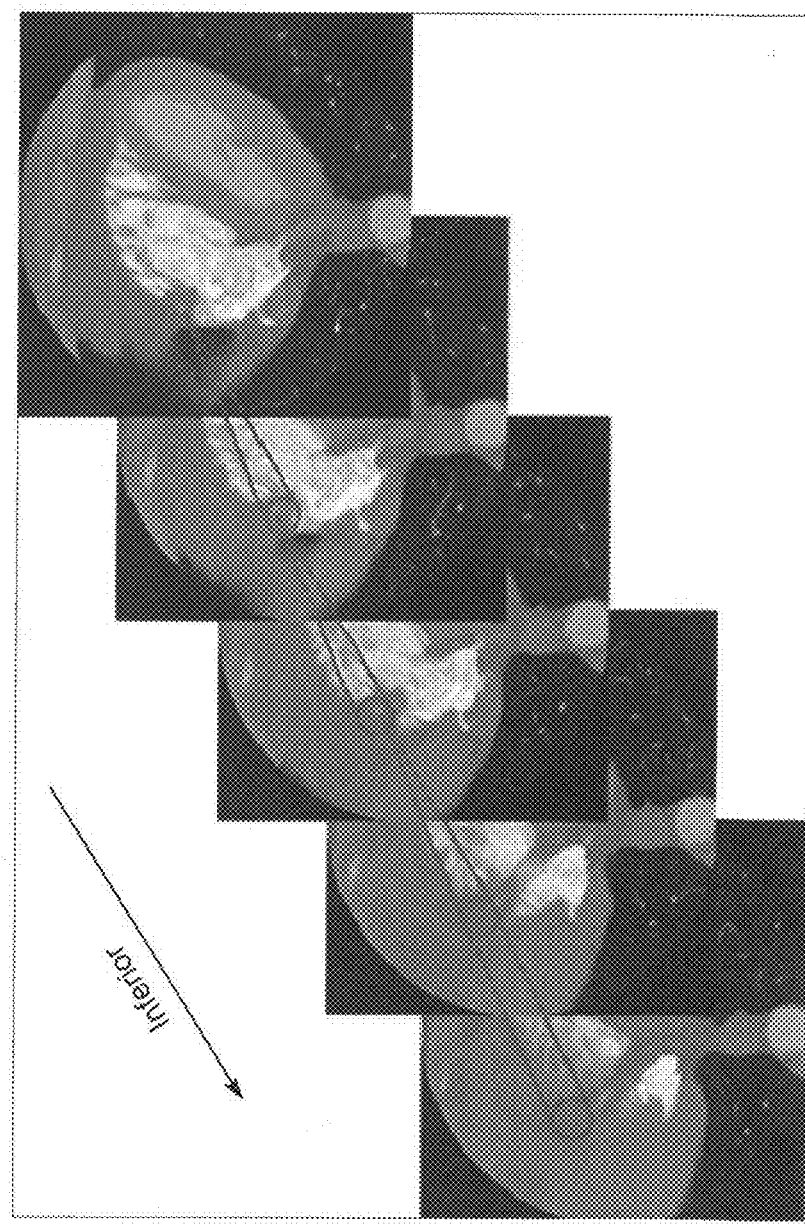
FIG. 23 illustrates an example of use of a recursive algorithm for searching for vessels in accordance with an embodiment.

A vessel map may be created. First, the location of through-plane vessels may be determined. Vessel maps are sets of potential vessel points that give the location of a through-plane vessel across multiple slices for a particular phase. Using vessel maps, the slices that contain through-plane vessels can be identified. In the depicted embodiment, for each phase, all potential vessel points from slices within 50 mm of the center of scan in the z-direction are considered starting points. Initially, slices directly above and below the starting point from the same phase are considered. For each potential vessel point in those slices, a line is drawn connecting the potential vessel point to the starting point. If the line connecting a potential vessel point to the starting point is at less than a 45° angle from the z-axis, the potential vessel point is added to the vessel map. The process continues recursively until two slices in a row cannot find a nearby potential vessel point (FIG. 23). Once this is repeated for all starting points, a list of potential vessels is available for a particular phase. In various embodiments, any potential vessels that span less than a predetermined length (e.g., 10 millimeters in the z-direction) may be discarded. This process may then be repeated for all phases.

Figure 24:
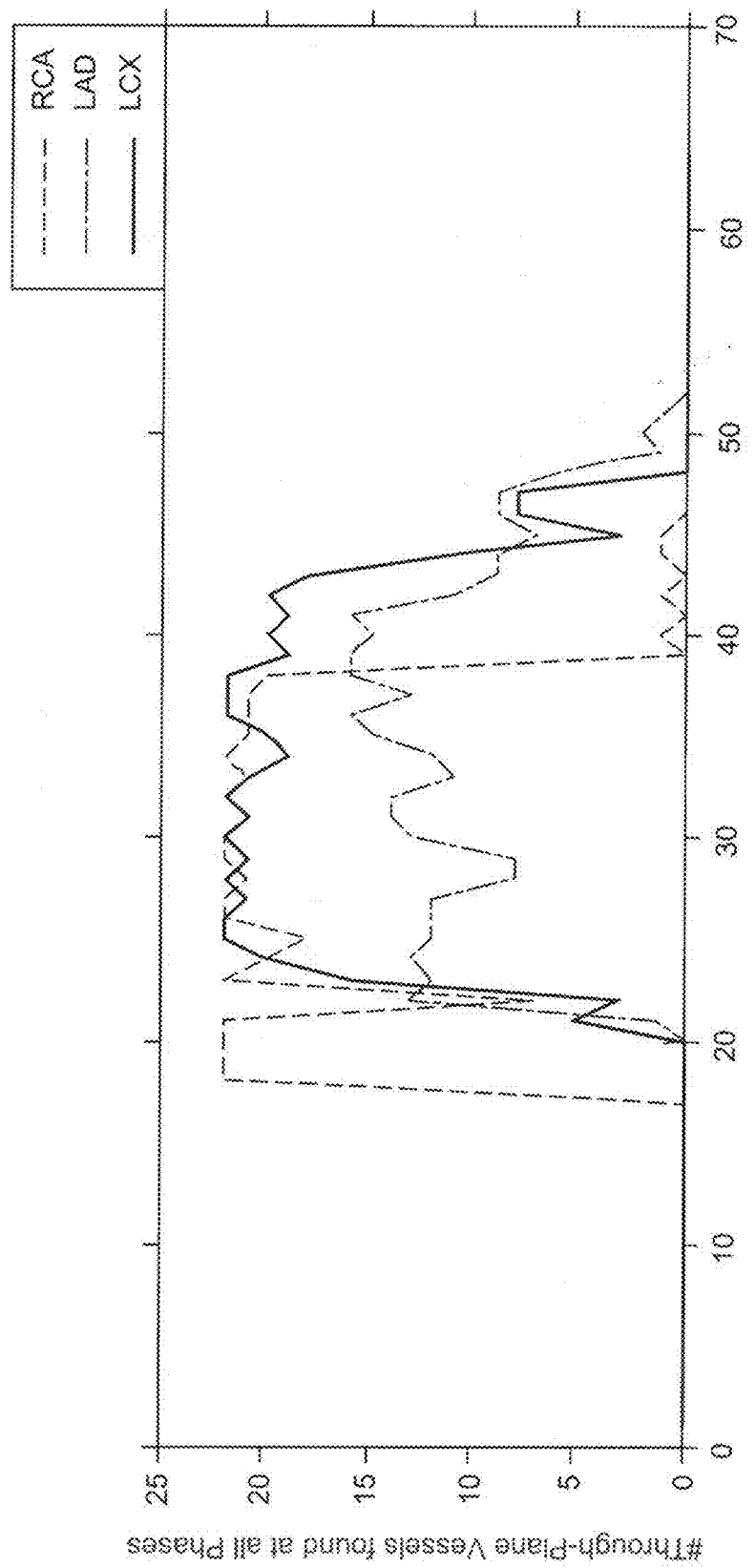
FIG. 24 provides a chart corresponding to located through-plane vessels in accordance with various embodiments.

Once vessel mapping has been completed for each phase, the results may be used to select slices that contain through-plane vessels in the most phases. The number of vessels that pass through the RCA, LAD, and LCX regions of each slice, determined by vessel mapping, are calculated and aggregated for all phases (FIG. 24). High values indicate that many different phases found a through-plane vessel. In the depicted embodiment, all slices with a value over 25% of the maximum are considered to have through-plane vessels.

Figure 25:
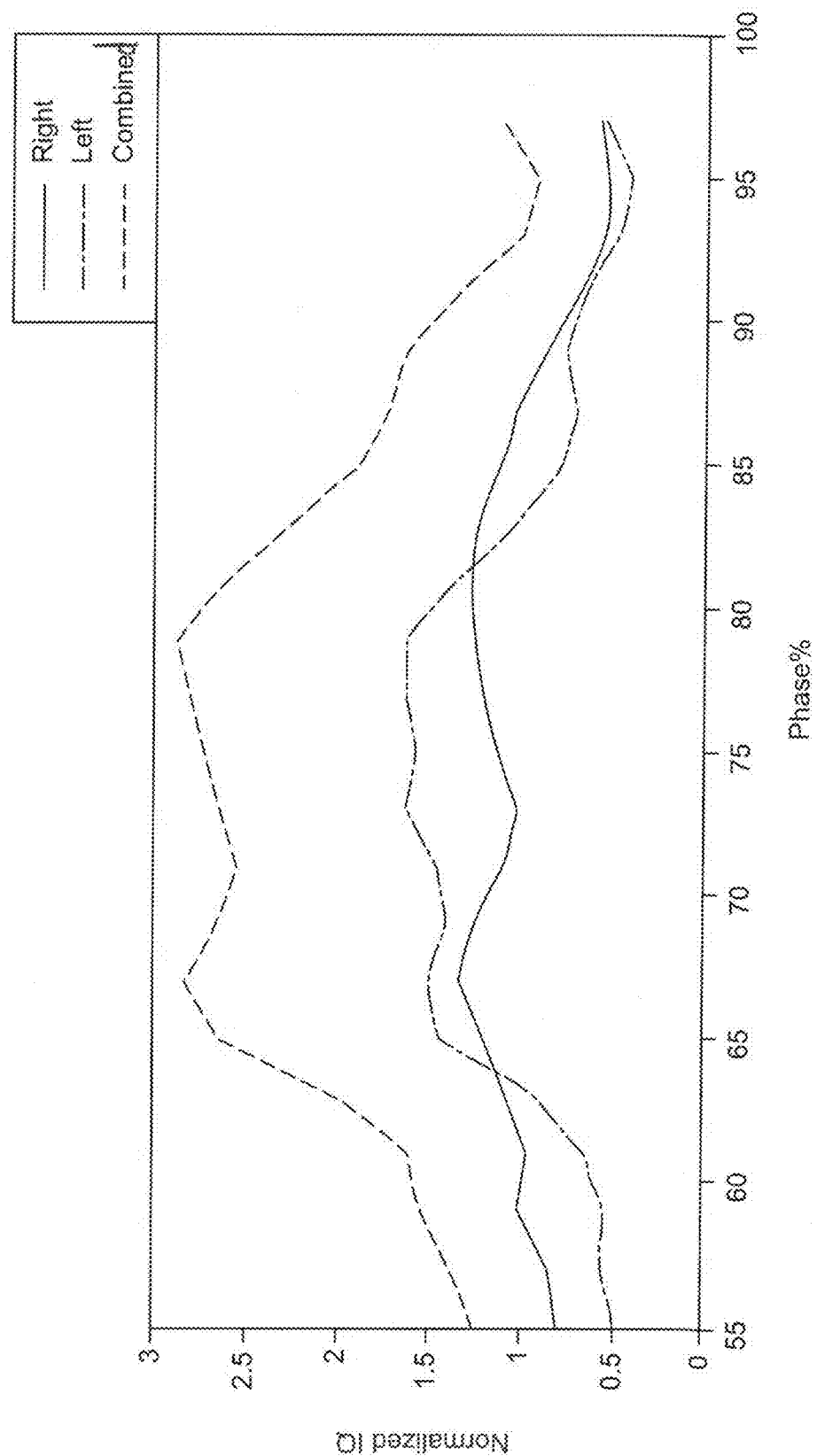
FIG. 25 provide a chart corresponding to IQ scores in accordance with various embodiments.

Returning to FIG. 13, in the fourth block 1340, the best phase for through-plane score is selected. At this point in the example algorithm, IQ has been calculated for each cardiac phase in all slices. The slices that contain through-plane vessels for each vessel have been identified. Next, the IQ metrics are summed across all slices that contain through-plane vessels. This gives an overall score of vessel IQ for each phase for the RCA, LAD, and LCX. The scores for the LAD and LCX are added to give an overall left side score. The best phase for each side is the phase with the largest IQ score on that side (FIG. 25). The results from the right and left sides are normalized by their mean and summed to find the overall IQ. It may be noted that, in various embodiments, alternative and/or additional steps or techniques to those discussed in connection with FIGS. 13-25 may be utilized to determine a through-plane score.

Figure 26:
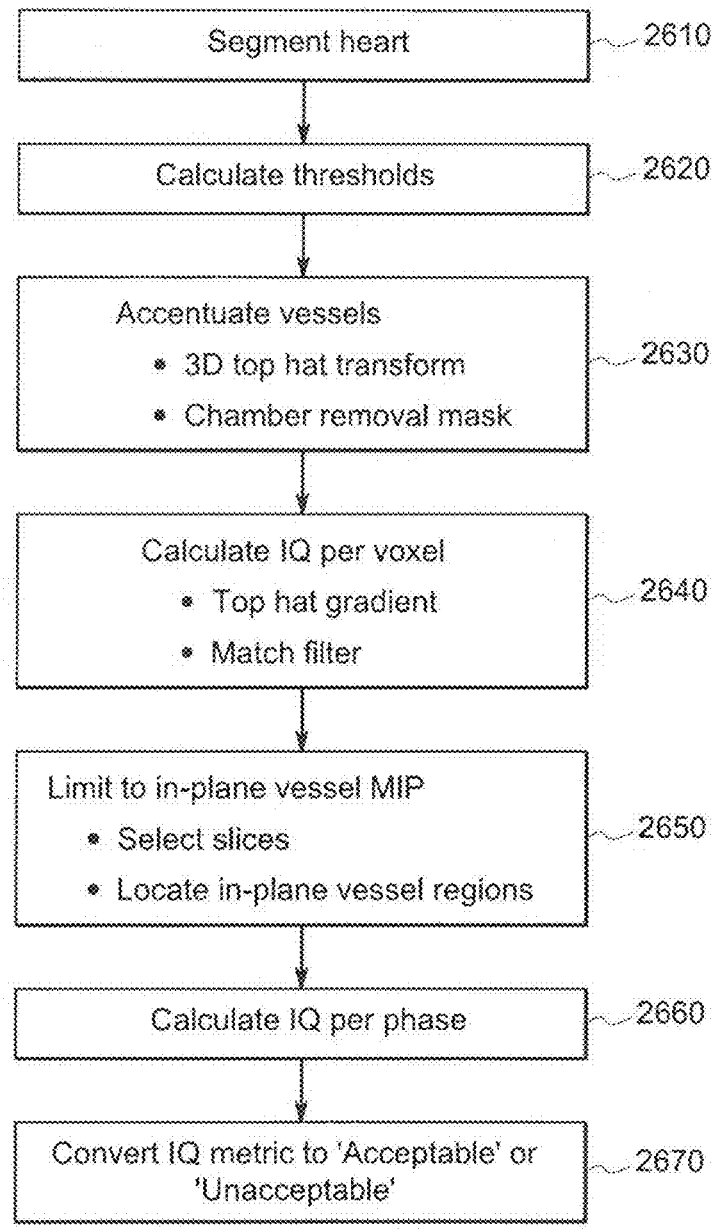
FIG. 26 illustrates a flowchart of a method for determining in-plane scores in accordance with various embodiments.

The determination of a through plane score in various embodiments will now be discussed, with particular reference to FIG. 26. In the illustrated embodiment, the in-plane metrics quantify or determine if the proximal left and right in-plane vessels are acceptable for a given candidate phase. For example, CT images reconstructed from the candidate phase as well as eight nearby phases may be input to the in-plane metric. Each slice from the superior half of the scan may be utilized to help ensure that the in-plane vessels are present for all phases and allow 3D image processing. Regions that contain in-plane vessels are identified in all phases, and a gradient-based IQ metric, similar to the edge score metric for the through-plane algorithm, is calculated. While, in various embodiments, the through-plane algorithm may assume a circular region with a single point per slice, the in-plane algorithm generally may determine the approximate vessel size and adjust to varying shapes and bifurcations. This metric is compared across phases to determine a binary score of 'Acceptable' or 'Unacceptable' for both the right and left vessels. A logical AND of the right and left vessel results gives the final determination of whether the in-plane vessels are 'Acceptable' at a given phase in the illustrated embodiment. A summary of the steps to calculate the in-plane score is shown in FIG. 26.

At 2610, the heart is segmented. Cardiac segmentation may be performed, for example, on each slice as discussed in connection with FIG. 13. Proximal in-plane vessels originate in the aorta and curve longitudinally as they near the edge of the heart. Therefore, only through-plane vessels will be present near the edge of the heart. To account for this, all pixels within a predetermined range (e.g., 6 millimeters) of the edge of the heart may be removed. This process is carried out in 2D for each axial slice at each phase. This step produces a mask that can be applied to limit the ROI to the heart.

At 2620, thresholds are calculated. For example, thresholds may be calculated in the same manner as for the through-plane metric discussed herein. However, the histogram for the in-plane metric may be created using volume data instead of slice data. The outputs of this step are a soft tissue threshold, a contrast threshold, and a maximum value threshold.

At 2630, vessels are accentuated. As part of accentuating vessels, the CT data may be manipulated to provide better contrast between the coronary arteries and other tissue. A top hat transform and chamber removal mask, similar to those used in the through-plane metric, may be applied to produce a volume for each phase that highlights small, high-valued regions and a mask that can be used to remove heart chamber locations.

For example, a three dimensional top hat transform may be applied. The structuring element may be spherical with a radius based on the average radius of the proximal coronaries and blurring due to motion and the point spread function in the CT. The proximal left coronary artery may have a diameter of 4.5±0.5 mm, while the proximal RCA may have a diameter of 3.9±0.6 mm. Allowing for a spread of ~5 mm, a radius of about 10 millimeters may be chosen for the structuring element. Accordingly, structures larger than about 20 millimeters in every dimension may be removed.

A 3D transform is advantageous because the longitudinal extents of large structures can be small in the axial plane and may therefore be retained with a 2D transform.

The chamber removal mask may be a multiplicative mask ranging from 0-1 that will remove heart chambers. This mask may be calculated for each axial slice as previously discussed in connection with the through-plane metric. However, the method to remove contrast swirling may not be implemented in connection with the in-plane metric, because it may also remove in-plane vessels connecting to the aorta.

Figure 27A:
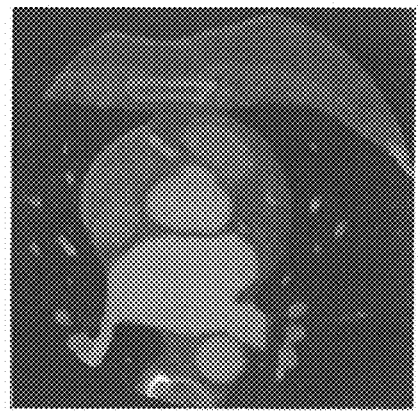
FIGS. 27A-D illustrate steps in in-plane voxel IQ calculations in accordance with various embodiments.
Figure 27B:
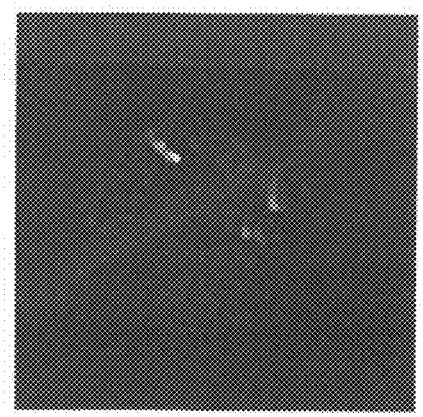
Figure 27C:
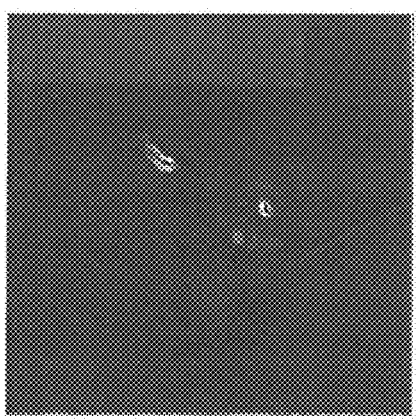
Figure 27D:
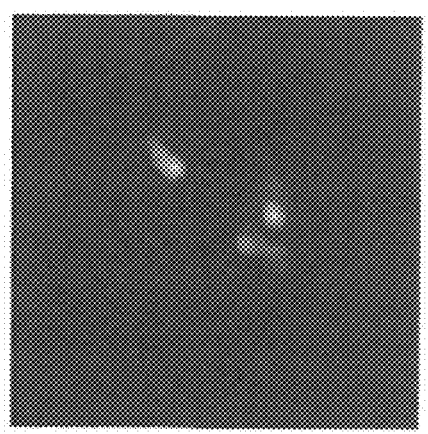

FIGS. 27A-D illustrates steps for an example in-plane voxel IQ calculation. FIG. 27A illustrates an original image, and FIG. 27B illustrates an example segmented top hat transform of the original image. FIG. 27C illustrates a top hat transform gradient multiplied by the chamber removal mask. FIG. 27D illustrates a final edge score after applying a match filter.

Returning to FIG. 26, at 2640, IQ is determined per voxel. A measure of IQ based on the gradient magnitude of each top hat image may be calculated. This metric is similar in certain respects to the edge strength score from the through-plane metric without the circularity assumption. A summary is shown in FIG. 27. This step produces a measure of in-plane vessel IQ at each voxel in each CT volume.

Further, the 2D gradient of each axial slice for each volume from 2630 may be calculated using a Sobel filter. A 2D gradient may be used instead of a 3D gradient in various embodiments, because thick slices may cause inaccurate gradient measurements. The gradient may next be multiplied by the chamber removal mask to ignore heart chambers.

Figure 28A:
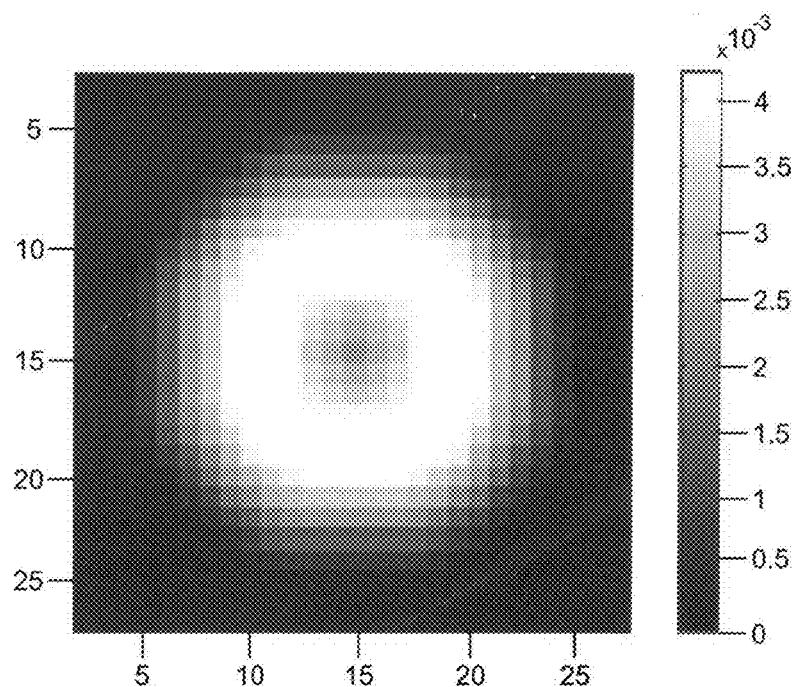
FIGS. 28A-B illustrate various aspects of a match filter in accordance with various embodiments.
Figure 28B:
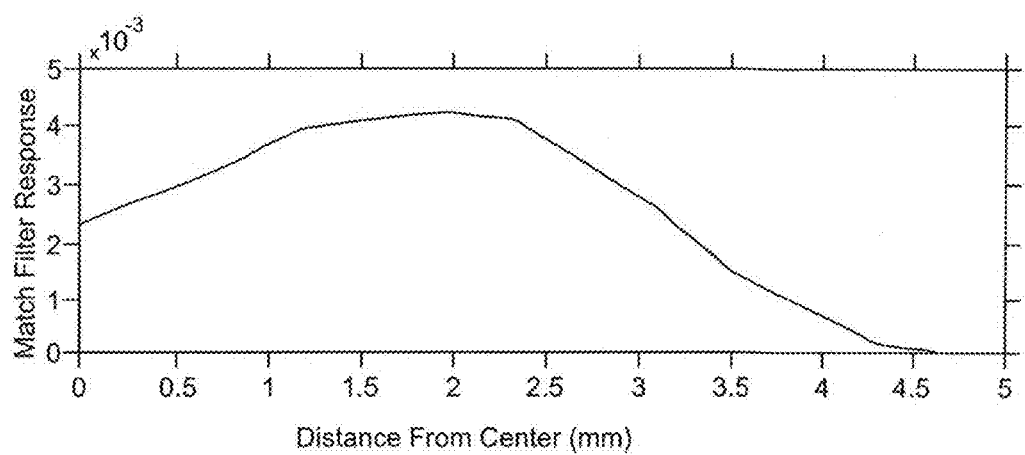

Next, a 2D match filter may be applied to each top hat gradient image. In some embodiments, the match filter may similar in design to the filter used in the through-plane metric with the negative lobes removed, because the negative lobes reduce output from non-circular regions. The positive lobe may be approximately 4.5 millimeters wide to encompass the entire vessel radius. Gradients of about 1.5-2.5 millimeters from the vessel center produce the strongest response, as this is the expected vessel radius. This filter may produce high values in the center of vessels with strong gradients. FIG. 28A illustrates an example match filter and FIG. 28B illustrates an example graph of match filter value based on distance from the center of the filter in millimeters.

Returning to FIG. 26, at 2650, voxel IQ data and cardiac segmentation results are next used to calculate a maximum intensity projection (MIP) of IQ scores with a projection straight down the longitudinal axis using only regions near in-plane vessels. Since vessels are in-plane, they should not travel underneath one another. If this were to happen, taking a MIP at this projection angle would cause information about the weaker overlapping vessel to be lost. Because vessels generally do not overlap, the dimensionality of the data is reduced without signal loss. To reduce noise, only slices that contain in-plane vessels may be used in the MIP in various embodiments. Once the MIP is calculated, only points near the vessel may be considered. This step uses IQ MIPs at each phase to provide approximate vessel sizes and locations for the right and left coronaries.

Selecting a small range of slices for MIP calculation reduces noise in the image and makes identification of in-plane vessels easier. The slices of interest vary between the right and left side, therefore a separate MIP may be created for each. The heart center may be determined generally in the same manner as discussed herein in connection with the through-plane metric. Since the proximal RCA originates from the anterior aorta, only points anterior to the heart center may be considered for the right side in various embodiments.

Figure 29A:
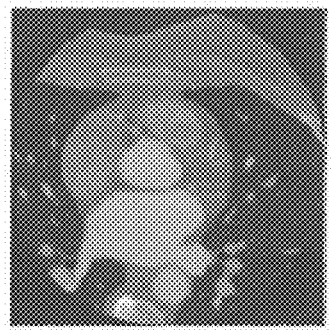
FIGS. 29A-F illustrate various aspects of slice selection in accordance with various embodiments.
Figure 29B:
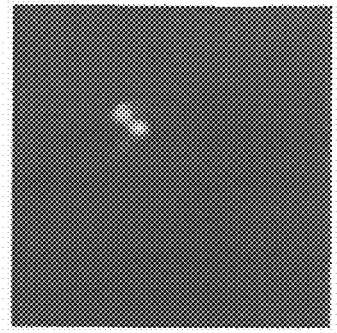
Figure 29C:
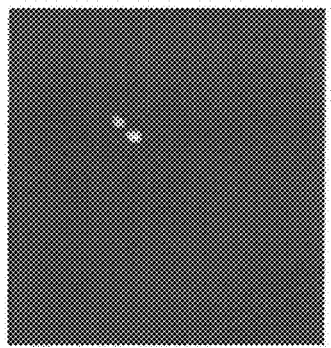
Figure 29D:
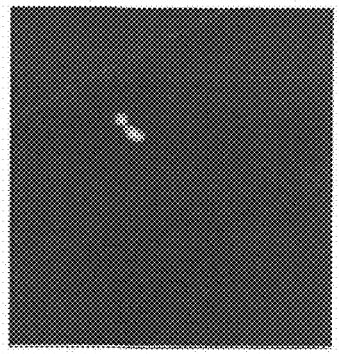
Figure 29E:
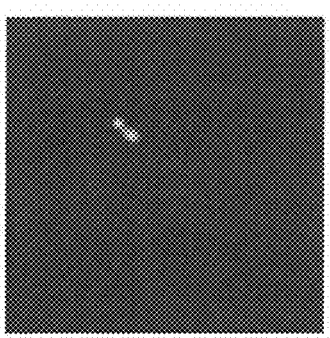

Slices that contain in-plane vessels may have many high-valued points. FIG. 29A illustrates an example original image near the proximal in-plane RCA, and FIG. 29B illustrates an IQ score limited to the anterior right quadrant. In the illustrated embodiment, low IQ scores may be removed by automatically thresholding using Otsu's method (FIG. 29C). A total of five contiguous slices (12.5 mm) may be chosen for each side. MIPs are calculated for the right and left sides with each possible combination of slices for each phase (FIG. 29D). Scores within each MIP are summed and these results are summed across all phases (FIG. 29E). This produces one score for each side with each set of slices. The in-plane vessels will be located in the set of slices with the highest total score. Therefore, an appropriate set of slices for each side may be identified.

Figure 29F:
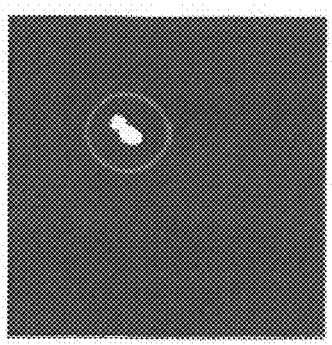

Next, the regions that contain in-plane vessels may be identified for all phases. Since a small range of phases (~20% of the cardiac cycle in some embodiments) is being used, the vessels may be in a similar location for all phases. Therefore, a single common region may be identified in some embodiments for the in-plane vessels for each side of the heart that will be used in all phases. A connected components algorithm with 8-connectivity may applied to locations where the thresholded MIP summed across all phases (FIG. 29E) is greater than zero. The largest region, circled in FIG. 29F, is selected as the location for the proximal in-plane RCA for all phases. Next, the size of the vessel is estimated for each phase. The number of pixels that are greater than zero in the thresholded MIP for each phase (FIG. 29D) logically ANDed with the estimated vessel location (FIG. 29F) is the size of the vessel at that phase. The average value across all phases is the estimated vessel size.

Figure 30A:
FIGS. 30A-D illustrate various aspects of MIP's in accordance with various embodiments.
Figure 30B:
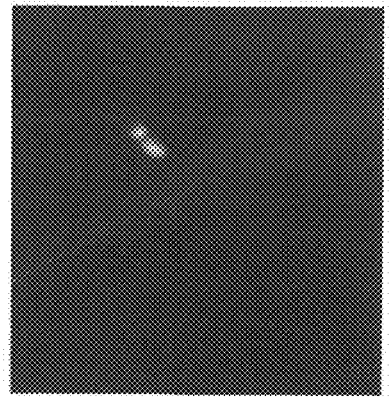
Figure 30C:
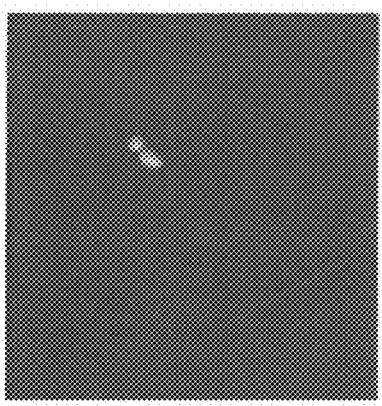
Figure 30D:
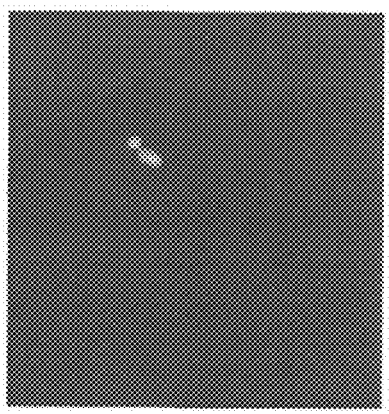
Figure 31:
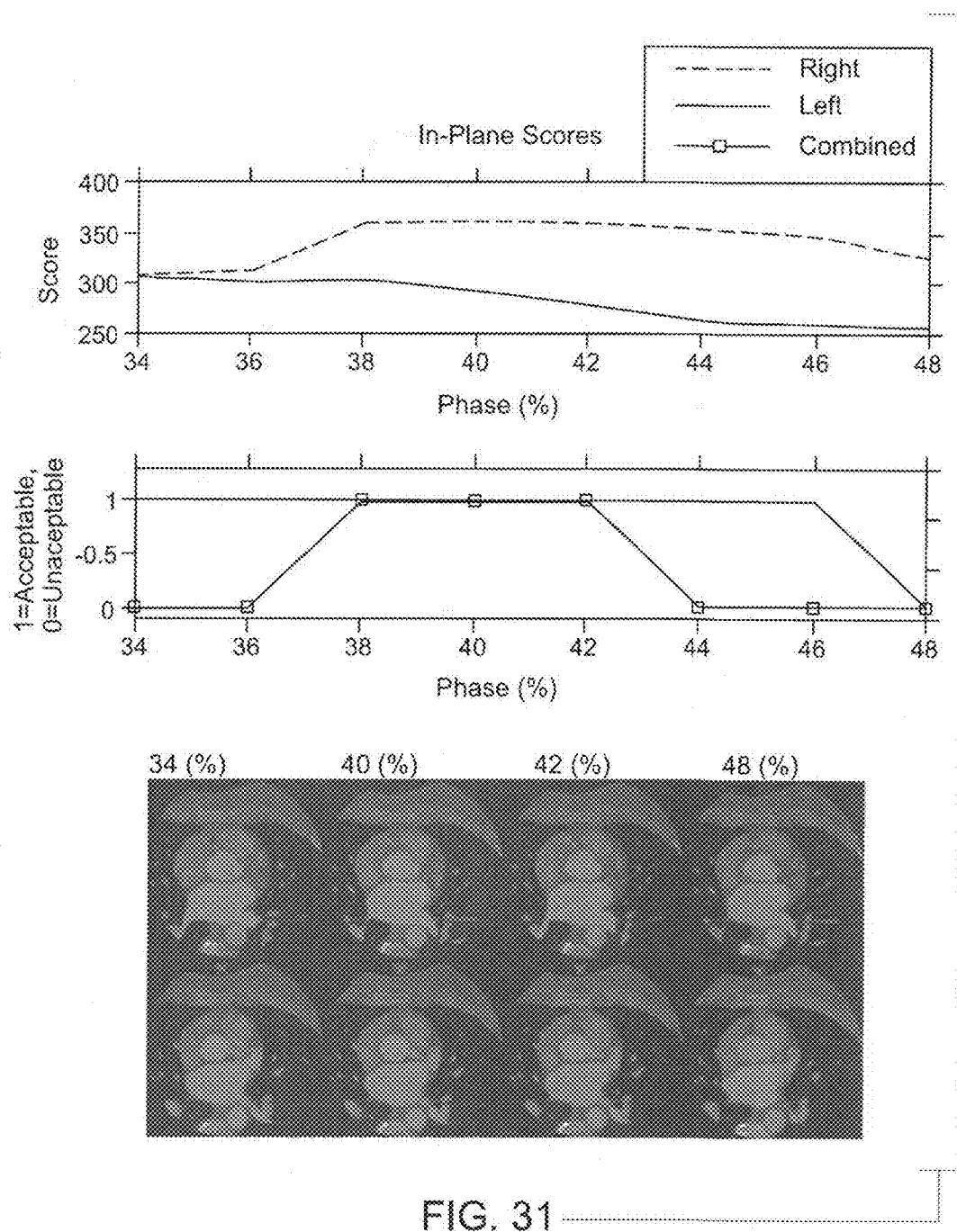
FIG. 31 illustrates aspects of IQ metrics in accordance with various embodiments.

Returning to FIG. 26, at 2660, IQ is calculated per phase. Slice locations, transverse locations, and the approximate size of in-plane vessels were provided at 2650. To calculate IQ at each phase, MIPs are calculated for each phase using the given slice locations using voxel IQ scores without applying Otsu's thresholding method. MIPs are limited to the identified transverse locations. The average score in each MIP from the top n highest valued points is the final IQ score for that phase where n is the estimated vessel size. This is repeated for each phase and each side of the heart. A summary of these steps is shown in FIGS. 30A-D) and the resulting scores are shown in FIG. 31. (FIG. 30A illustrates an original image near the proximal in-plane RCA, FIG. 30B illustrates an unthresholded MIP for the given phase across five slices surrounding the slice from FIG. 30A, FIG. 30C illustrates an unthresholded MIP limited to the proximal RCA region, and FIG. 30D illustrates points selected to limit the estimated vessel size.)

At 2670, the IQ metric is converted to an "Acceptable" or "Unacceptable" value. In-plane IQ scores determined at 2660 are converted to binary to determine if the candidate phase has 'Acceptable' in-plane vessel IQ. This is done by comparing the candidate phase score to the scores at nearby phases. A hard IQ score threshold may not be used in various embodiments because the magnitude of the score depends heavily on image contrast, including the presence of calcifications. If vessels are not found in most phases for a particular side of the heart, the in-plane score may be considered unreliable. In this case, the IQ of in-plane vessels may be unknown for a given side of the heart and all phases may be considered to have 'Acceptable' results for the in-plane metric, so that the phase having the best through-plane metric is selected as the best phase. Otherwise, in some embodiments, IQ scores are normalized by the mean and an adjustable acceptability threshold, typically ~0.90, may be applied to each side. This determines if the results are acceptable at each phase separately for the right and left side. A logical AND is used to combine the binary metrics from the right and left sides, identifying phases where both sides contain vessels that are 'Acceptable'. An example of in-plane scores and their conversion to a binary metric is shown in 31. In FIG. 31, for example, the phase of 40% may be identified as a candidate phase and selected due to having acceptable binary in-plane metrics for both right and left sides.

It should be noted that the various flowcharts and discussion herein are meant by way of example and not limitation. The methods described herein, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the methods described herein may be able to be used as one or more algorithms to direct hardware to perform one or more operations described herein.

An algorithm as described in connection with FIG. 17-31 was evaluated using a number of single-beat datasets. The algorithm was found to be statistically equivalent to a reader in selecting the optimal cardiac phase for CCTA exams.

Figure 32:
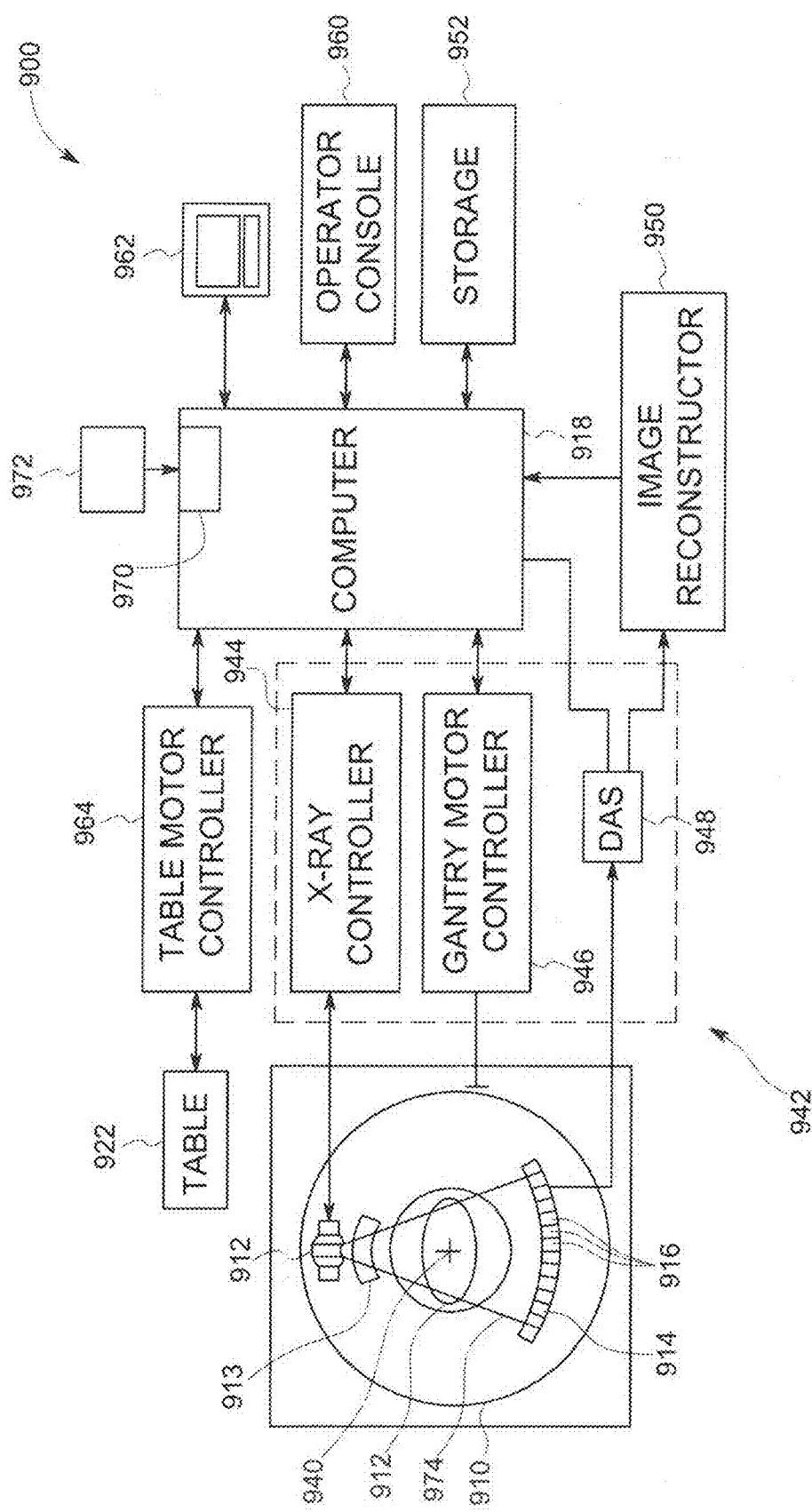
FIG. 32 provides a schematic diagram of a CT imaging system in accordance with various embodiments.

Various methods and/or systems (and/or aspects thereof) described herein may be implemented using a medical imaging system. For example, FIG. 32 is a block schematic diagram of an exemplary CT imaging system 900 that may be utilized to implement various embodiments discussed herein. Although the CT imaging system 900 is illustrated as a standalone imaging system, it should be realized that the CT imaging system 900 may form part of a multi-modality imaging system. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module 915 are provided proximate the X-ray source 912. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

As discussed above, the detector 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 9 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view". A "scan" of the subject 917 comprises a set of views made at different gantry angles, or view angles, during one or more revolutions of the X-ray source 912 and the detector 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method comprising:
generating corresponding intermediate images for each phase of at least one range of phases of a cardiac cycle;
determining a first image quality (IQ) metric for the intermediate images corresponding to IQ of through-plane vessels;
determining a second IQ metric for at least one of the intermediate images corresponding to IQ of in-plane vessels; and
selecting a selected phase from the at least one range of phases based on the first IQ metric and the second IQ metric for the intermediate images.

2. The method of claim 1, wherein the second IQ metric is converted to one of an acceptable or unacceptable value based on a threshold.

3. The method of claim 2, wherein a phase having a highest first IQ metric value while having an acceptable second IQ metric value is selected as the selected phase.

4. The method of claim 1, further comprising determining the at least one range of phases of a cardiac cycle from which to select the selected phase based on at least one of patient demographic information, patient physiological information, or a general physiological model.

5. The method of claim 1, wherein the first IQ metric corresponds to at least one of circularity or edge strength.

6. The method of claim 1, wherein the second IQ metric corresponds to edge strength.

7. The method of claim 1, further comprising reconstructing a final image of the selected phase, wherein the intermediate images have a resolution that is lower than a resolution of the final image.

8. The method of claim 1, further comprising:
determining if at least one of the first IQ metric and the second IQ metric satisfy a threshold;
performing motion correction for the selected phase if the threshold is not satisfied; and
not performing motion correction for the selected phase if the threshold is satisfied.

9. An imaging system comprising:
an acquisition unit comprising an X-ray source and a computed tomography (CT) detector; and
at least one processing unit operably coupled to the acquisition unit and configured to acquire CT imaging information from the acquisition unit, the at least one processing unit further configured to:
determine at least one range of phases of a cardiac cycle from which to select a selected phase based on at least one of patient demographic information, patient physiological information, or a general physiological model;
generate corresponding intermediate images for each of the phases of the at least one range of phases using the CT imaging information;
determine, on a phase by phase basis independently for each of the phases, a first IQ metric for the intermediate images corresponding to IQ of through-plane vessels;
determine, on a phase by phase basis, a second IQ metric for at least one of the intermediate images corresponding to IQ of in-plane vessels;
select the selected phase based on the first IQ metric and the second IQ metric of the intermediate images; and
reconstruct an image for diagnostic use using imaging information from the selected phase.

10. The imaging system of claim 9, wherein the at least one processing unit is configured to operate the acquisition unit to acquire CT imaging information over a first range corresponding to the determined at least one range of phases, and to not acquire CT imaging information over a second range corresponding to a range of phases not included in the determined at least one range of phases.

11. The imaging system of claim 9, wherein the intermediate images have a resolution that is lower than a resolution of the image reconstructed for diagnostic use.

12. The imaging system of claim 9, wherein the at least one processing unit is configured to:
determine if at least one IQ metric satisfies a threshold;
perform motion correction for the selected phase if the threshold is not satisfied; and
not perform motion correction for the selected phase if the threshold is satisfied.

13. The imaging system of claim 9, wherein the at least one processing unit is further configured to select, as the selected phase, a phase having a highest first IQ metric value while having an acceptable second IQ metric value.

* * * * *